US006835866B1

(12) United States Patent
Mangelsdorf et al.

(10) Patent No.: US 6,835,866 B1
(45) Date of Patent: Dec. 28, 2004

(54) COMPOSITIONS AND METHODS OF MODULATING CHOLESTEROL METABOLISM

(75) Inventors: David J. Mangelsdorf, Dallas, TX (US); Joyce J. Repa, Dallas, TX (US); Stephen D. Turley, Dallas, TX (US); John M. Dietschy, Dallas, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 09/460,292

(22) Filed: Dec. 10, 1999

Related U.S. Application Data

(60) Provisional application No. 60/111,894, filed on Dec. 10, 1998.

(51) Int. Cl.[7] .......................... C12P 21/00; A01K 67/00; A01K 67/027; C12N 5/00

(52) U.S. Cl. ............................... 800/18; 800/4; 800/8; 800/9; 800/13; 435/325

(58) Field of Search ............................. 800/8, 21, 18, 800/4, 9, 13; 435/325, 455

(56) References Cited

U.S. PATENT DOCUMENTS

| | | | |
|---|---|---|---|
| 4,430,434 A | 2/1984 | Sanders et al. | 435/253 |
| 4,559,302 A | 12/1985 | Ingolia | 435/172.3 |
| 4,727,028 A | 2/1988 | Santerre et al. | 435/240.2 |
| 4,960,704 A | 10/1990 | Ingolia et al. | 435/252.33 |
| 5,354,855 A | 10/1994 | Cech et al. | 536/24.1 |
| 5,697,899 A | 12/1997 | Hillman et al. | 604/28 |
| 5,779,708 A | 7/1998 | Wu | 606/80 |
| 5,780,676 A | 7/1998 | Boehm et al. | 562/490 |
| 5,783,208 A | 7/1998 | Venkateshwaran et al. | 424/448 |
| 5,789,655 A | 8/1998 | Prusiner et al. | 800/2 |
| 5,797,898 A | 8/1998 | Santini, Jr. et al. | 604/890.1 |

FOREIGN PATENT DOCUMENTS

EP 0273085 12/1986

OTHER PUBLICATIONS

R.W. Moreadith et al., Mol Med (1997)75:208–216.*
M. Beato et al., Cell, vol. 83,Dec. 1995, pp. 851–857.*
R.F. Seamark, Reprod. Fertil.Dev., 1994,6, 653–657.*
R. Evans, Science, May 1988, vol. 240, pp. 889–895.*
D. Mangelsdorf et al., Cell, vol. 83, Dec. 1995, pp. 841–850.*
Accad and Farese Jr.,"Cholesterol homeostasis: a role for oxysterols". Curr. Biol. 8:R601–R604, 1998.
Androlewicz et al.,"Characteristics of peptide and major histocompatibility complex class I/$\beta_2$–microglobulin binding to the transporters associated with antigen processing (TAP1 and TAP2)," Proc.Natl. Acad. Sci. USA 91:12716–12720, 1994.

Bodzioch et al. "The gene encoding ATP–binding cassette transporter 1 is mutated in Tangier disease," Nat. Genet. 22:347–351, 1999.

Boehm et al.,"Design and synthesis of potent retinoid X receptor selective ligands that induce apoptosis in leukemia cells." J. Med. Chem. 38:3146–3155, 1995.

Brooks–Wilson et al. "Mutations in ABC1 in Tangier disease and familial high–density lipoprotein deficiency," Nat. Genet. 22:336–345, 1999.

Brown and Goldstein, "The SREBP pathway: regulation of cholesterol metabolism by proteolysis of a membrane–bound transcription factor," Cell, 89:331–340, 1997.

Buchler et al.,"cDNA cloning of the hepatocyte canalicular isoform of the multidrug resistance protein, cMrp, reveals a novel conjugate export pump deficient in hyperbilirubinemic mutant rats," J. Biol. Chem. 271(25):15091–15098, 1996.

Bugge et al., "RXR$\alpha$, a promiscuous partner of retinoic and thyroid hormone receptors," EMBO J., 11(4):1409–1418, 1992.

Chiang and Stroup, "Identification and characterization of a putative bile acid–responsive element in cholesterol 7$\alpha$–hydroxylase gene promoter," J. Biol. Chem., 269(26):17502–17507, 1994.

Field et al.,"Caveolin is present in intestinal cells: role in cholesterol trafficking?" J. Lipid Res. 39:1938–1950, 1998.

Forman et al., "Unique response pathways are established by allosteric interacions among nuclear hormone receptors," Cell, 81:541–550, 1995.

Forman et al., Cell, "Identification of a nuclear receptor that is activated by farnesol metabolites," 81:687–693, 1995.

(List continued on next page.)

Primary Examiner—Joseph Woitach
(74) Attorney, Agent, or Firm—Fulbright & Jaworski

(57) ABSTRACT

The present invention relates to compositions and methods for reducing cholesterolemia and its effects. More specifically, the invention is directed, in one embodiment, to methods for screening for compounds that affect cholesterol levels generally, and in particular, that affect the absorption of cholesterol. The invention also is directed to methods of screening for compounds that increase bile acid synthesis. In so doing, the inventors describe useful transgenic cells and animals which lack one or both alleles of the LXR$\alpha$ gene. Also provided are therapeutic methods designed to reduce cholesterol levels in suitable subjects. The reduction may be effected by decreasing cholesterol absorption, increasing bile acid synthesis, or combinations thereof. Particularly useful in decreasing cholesterol absorption are RXR agonists, for example, rexinoid compounds. Therapeutic intervention in cholesterol biosynthesis and diet are additional adjunct therapies. In addition, the present invention relates to candidate compounds that modulate the expression of ABC-1 in a cell that expresses RXR. Methods of identifying and making a modulator of ABC-1 are disclosed.

21 Claims, 10 Drawing Sheets

OTHER PUBLICATIONS

Forman et al., "15–Deoxy–$\Delta^{12,\ 14}$–prostaglandin $J_2$ is a ligand for the adipocyte determination factor PPARγ," *Cell*, 83(5):803–812, 1995b.

Forman et al., "A domain containing leucine–zipper–like motifs mediate novel in Vivo interactions between the thyroid hormone and retinoic acid receptors," *Mol. Endocrinol.*, 3:(10)1610–1626, 1989.

Francis et al., "Defective removal of cellular cholesteral and phospholipids by apolipoprotein A–1 in Tangier disease," *J. Clin. Invest*. 96:78–87,1995.

Glass, "Differential recognition of target genes by nuclear receptor monomers, dimers, and heterodimers," *Endocrine Rev.*, 15(3):391–407, 1994.

Hersdorffer et al., "Efficient gene transfer in live mice using a unique retroviral packaging line," *DNA Cell Biol.*, 9(10):713–723, 1990.

Higgins, "ABC transporters: from microorganisms to man," *Annu. Rev. Cell Biol.* 8:67–113, 1992.

Homan and Krause, "Established and emerging strategies for the inhibition of cholesterol absorption." *Curr. Pharmaceut. Design* 3:29–44, 1997.

Ishibashi et al., "Hypercholesterolemia in low density lipoprotein receptor knockout mice and its reversal by adenovirus–mediated gene delivery," *J. Clin. Invest.*, 92:883–893, 1993.

Ishibashi et al., "Disruption of cholesterol 7α–hydroxylase gene in mice. I. Postnatal lethality reversed by bile acid and vitamin supplementation," *J. Biol. Chem.*, 271(30):18017–18023, 1996.

Janowski et al., "An oxysterol signaling pathway mediated by the nuclear receptor LXRα," *Nature*, 383:728–731, 1996.

Kliewer et al., "Convergence of 9–cis retinoic acid and peroxisome proliferater signalling pathways through heterodimer formation of their receptors," *Nature*, 358:771–774, 1992.

Kliewer et al., "Retinoid X receptor interacts with nuclear receptors in retinoic acid, thyroid hormone and vitamin $D_3$ signalling," *Nature*, 355: 446–449, 1992.

Kliewer et al., "Differential expression and activation of a family of murine peroxisome proliferator–activated receptors," *Proc. Natl. Acad. Sci. USA*, 91:7355–7359, 1994..

Kurokawa et al., "Differential orientations of the DNA–binding domain and carboxy–terminal dimerization interface regulate binding site selection by nuclear receptor heterodimers," *Genes Dev.*, 7:1423–1435, 1993.

Kurokawa et al., "Regulation of retinoid signalling by receptor polarity and allosteric control of ligand binding," *Nature*, 371:528–531, 1994.

Kurokawa et al., "Polarity–specific activities of retinoic acid receptors determined by a co–repressor," *Nature*, 377:451–454, 1995.

Langmann et al. "Molecular cloning of the human ATP–binding cassette transporter 1 (hABC1): evidence for sterol–dependent regulation in macrophages," *Biochem. Biophys. Res. Commun.* 257:29–33, 1999.

Lawn et al. "The Tangier disease gene product ABC1 controls the cellular apolipoprotein–mediated lipid removal pathway," *J. Clin. Invest.* 104:R25–R31, 1999.

Leblanc & Stunnenberg, "9–Cis retinoic acid signaling: changing partners causes some excitement," *Genes Dev.*, 9:1811–1816, 1995.

Lehmann et al., "Activation of the nuclear receptor LXR by oxysterols defines a new hormone response pathway," *J. Biol. Chem.*, 272(6):3137–3140, 1997.

Lehrman et al., "Alu–Alu recombination deletes splice acceptor sites and produces secreted low density lipoprotein receptor in a subject with familial hypercholesterolemia," *J. Biol. Chem.*, 262(7):3354–3361, 1987.

Leid et al, "Purification, cloning, and RXR identify of the HeLa a cell factor with which RAR or TR heterodimerizes to bind target sequences efficiently," *Cell*, 68:377–395, 1992.

Leid et al., "Multiplicity generates diversity in the retinoic acid signalling pathways," *Trends Biochem Sci.*, 17:427–433, 1992.

Mangelsdorf et al., "A direct repeat in the cellular retinol–binding protein type 11 grene confers differential regulation by RXR and RAR," *Cell*, 66:555–561, 1991.

Mangelsdorf et al., "Characterization of three RXR genes that mediate the action of 9–cis retinoic acid," *Genes Dev.*, 6:329–344, 1992.

Mangelsdorf et al., "Nuclear receptor that identifies a novel retinoic acid response pathway," *Nature*, 345:224–229, 1990.

Marks et al., "H–2RIIBP (RXRβ) heterodimerization provides a mechanism for combinatorial diversity in the regulation of retinoic acid and thyroid hormone responsive genes," *EMBO J.*, 11(4):1419–1435, 1992.

McNeish et al., "High density lipoprotein deficiency and foam cell accumulation in mice with targeted disruption of ATP–binding cassette transporter–1," *PNAS*, 97(8): 4245–4250, 2000.

Mori et al., "Molecular cloning and deduced amino acid sequence of nonspecific lipid transfer protein (sterol carrier protein 2) of rat liver: a higher molecular mass (60 kDa) protein contains the primary sequence of nonspecific lipid transfer protein as its C–terminal part," *Proc. Natl. Acad. Sci. USA*, 88:4338–4342, 1991.

Orso et al, "Transport of lipids from Golgi to plasma membrane is defective in Tangier disease patients and Abcl–deficient mice," *Nature Genetics*, 24:192–196, 2000.

Osono et al., "Role of the low density lipoprotein receptor in the flux of cholesterol through the plasma and across the tissue of the mouse," *J. Clin. Invest.*, 95:1124–1132, 1995.

Peet et al.,"The LXRs: a new class of oxysterol receptors," *Curr. Opin. Genet. Dev.* 8:571–575, 1998.

Peet et al.,"Cholesterol and bile acid metabolism are impaired in mice lacking the nuclear oxysterol receptor LXRα," *Cell* 93:693–704, 1998.

Perlmann & Jansson, "A novel pathway for vitamin A signaling mediated by RXR heterodimerization with NGFI–B and NURR1," *Genes Dev.*, 9:769–782, 1995.

Perlamnn et al., "Determinants for selective RAR and TR recognition of direct repeat HREs," *Genes Dev.*, 7:1411–1422, 1993.

Repa and Mangelsdorf, "Nuclear receptor regulation of cholesterol and bile acid metabolism," *Curr. Opin. in Biotech.*, 10: 557–563, 1999.

Rudling, "Hepatic mRNA levels for the LDL receptor and HMG–CoA reductase show coordinate regulation in vivo," *J. Lipid Res.*, 33:493–501, 1992.

Russell and Setchell, "Bile acid biosynthesis," *Biochemistry*, 31(20): 4737–4749, 1992.

Rust et al., "Tangier disease is caused by mutations in the gene encoding ATP–binding cassette transporter 1," *Natural Genetics*, 22: 352–355, 1999.

Savary et al.,"Isolation and chromasonal mapping of a novel ATP–binding cassette transporter conserved in mouse and human," *Genomics* 41:275–275, 1997.

Schwarz et al.,"Marked reduction in bile acid synthesis in cholesterol 7α–hydroxylase–deficient mice does not lead to diminished tissue cholesterol turnover or to hypercholesterolemia," *J. Lipid Res.* 39:1833–1843, 1998.

Shimano et al.,"Overproduction of cholesterol and fatty acids causes massive liver enlargement in transgenic mice expressing truncated SREBP–la," *J. Clin. Invest.*, 98(7):1575–1584, 1996.

Shimano et al.,"Elevated levels of SREBP–2 and cholesterol synthesis in livers of mice homozygous for a targeted disruption of the SREBP–1 gene," *J. Clin. Invest.*, 100(8):2115–2124, 1997.

Tall, "An overview of reverse cholesterol transport," *Eur. Heart J.* 19(Suppl. A): A31–A35, 1998.

Turley and Dietschy, "The metabolism and excretion of cholesterol by the liver," *In: The Liver Biology and Pathobiology*, Arias, Jakoby, Popper, Schachter, Shafritz (eds.), New York: Raven Press, Ltd., pp. 617–641, 1988.

Turley et al.,"Psyllium augments the cholesterol–lowering action of cholestryramine in hamsters by enhancing sterol loss from the liver," *Gastroenterology*, 107:444–452, 1994.

Turley et al., "Cholesterol–lowering action of psyllium mucilloid in the hamster: sites and possible mechanisms of action," *Metabolism*, 40(10):1063–1073, 1991.

Turley et al., "Effect of feeding psyllium and cholestyramine in combination on low density lipoprotein metbolism and fecal bile acid excretion in hamsters with dietary–induced hypercholesterolemia," *J. Cardiovasc. Pharmacol.* 27:71–79, 1996.

Turley et al., "Regulation of fecal bile acid excretion in male Golden Syrian hamsters fed a cereal–based diet with an without added cholesterol," *Hepatology*, 25:797–803, 1997.

Wahlstrom et al.,"Binding characteristics of the thyroid hormone receptor homo–and heterodimers to consensus AGGTCA repeat motifs," *Mol. Endocrinol.*, 6:1013–1022, 1992.

Willy and Mangelsdorf, "Nuclear orphan receptors: The search for novel ligands and signalling pathways," *Hormones and Signaling*, 1: 307–358, 1998.

Willy et al. "LXR, a nuclear receptor that defines a distinct retinoid response pathway," *Genes Dev.*, 9:1033–1045, 1995.

Yeom et al., "Germline regulatory element of Oct–4 specific for the totipotent cycle of embryonal cells," *Development*, 122:881–894, 1996.

Yokode et al., "Diet–induced hypercholesterolemia in mice: prevention by overexpression of LDL receptors," *Science*, 250:1273–1275, 1990.

Young and Fielding, "The ABCs of cholesterol efflux," *Nature Genetics* 22: 316–318, 1999.

Yu et al.,"RXRβ: A coregulator that enhances binding of retinoic acid, thyroid hormone, and vitamin D receptors to their cognate response elements," *Cell*, 67:1251–1266, 1991.

Zechel et al., "The dimerization interfaces formed between the DNA binding domains of RXR, RAR and TR determine the binding specificity and polarity of the full–length receptors to direct repeats,", *EMBO J.*, 13(6):1425–1433, 1994.

Zhang et al., "Retinoid X receptor is an auxiliary protein for thyroid hormone and retinoic acid receptors," *Nature*, 355:441–446, 1992.

* cited by examiner

COMPOSITIONS AND METHODS OF MODULATING CHOLESTEROL METABOLISM

The present application claims the benefit of U.S. Provisional Patent Application, Ser. No. 60/111,894, filed Dec. 10, 1998.

BACKGROUND OF THE INVENTION

A. Field of the Invention

The present invention relates generally to the fields of biochemistry and molecular biology. More particularly, it relates to lipid metabolism and the regulation of lipid metabolism. In a specific embodiment, it relates to inhibition of intestinal absorption of cholesterol by ligands that bind to the retinoid X nuclear hormone receptor (RXR).

B. Description of Related Art

Sterols are structural lipids present in the membranes of most eukaryotic cells. These lipids are rigid and characterized by a four ring hydrocarbon steroid nucleus. Sterols are required not only to impart membrane fluidity, but also serve as the precursors for a variety of products with specific biological activities. For example, cholesterol, an amphipathic sterol with a polar hydroxyl head group and nonpolar hydrocarbon body (the steroid nucleus), is the major sterol found in animal tissues. Cholesterol is an essential molecule, playing a critical role in the structural integrity of cell membranes, a precursor for steroid hormones and serves as a precursor for bile acids. Cholesterol is synthesized in the liver from isoprene precursors and further obtained via dietary intake.

Although cholesterol is a requisite molecule, high levels of blood cholesterol or hypercholesterolemia has been implicated in atherosclerosis, heart attack, and stroke (Schultheis, 1990; Mitchell, 1990). Hypercholesterolemia, if not controlled, is one of several conditions that can lead to coronary artery disease. Coronary artery disease is the leading cause of death in the United States, accounting for approximately 600,000 deaths per year. Thus, the need exists for methods of treatment that can reduce cholesterol levels and methods to screen patients at risk for high cholesterol.

Possible targets for treatment are transcription factors involved in cholesterol metabolism. One such set of factors, nuclear receptors, are ligand-activated transcription factors that govern aspects of every major developmental and metabolic pathway (reviewed in Kastner et al., 1995; Mangelsdorf et al., 1995). For example, the LXRs were first identified as "orphan" members of the nuclear receptor superfamily whose ligands and functions are unknown (Willy and Mangelsdorf, 1998). The LXRs have recently been shown to be activated by a specific class of naturally occurring, oxidized derivatives of cholesterol, including 22(R)-hydroxycholesterol, 24(S)-hydroxycholesterol, and 24,25(S)-epoxycholesterol (Janowski et al., 1996; Lehmann et al., 1997). Oxysterols are concentrated in tissues where cholesterol metabolism and LXR expression are high, such as liver, brain, and placenta (Lavy et al., 1977; Spencer et al., 1985; Lütjohann et al., 1996).

LXRs function as heterodimers with the retinoid X receptors (RXRs), and thus, the RXR/LXR complex can be activated by both RXR ligands (i.e., rexinoids) and oxysterols (Teboul et al., 1995; Willy et al., 1995; Janowski et al., 1996). Two LXR proteins ($\alpha$ and $\beta$) are known to exist in mammals. The expression of LXR$\alpha$ is restricted, with highest levels in the liver (hence, the name liver X receptor) and lower but significant levels in kidney, intestine, spleen, and adrenals (Apfel et al., 1994; Willy et al., 1995). LXR$\beta$ expression is more widespread and has been found in nearly every tissue examined (Shinar et al., 1994; Song et al., 1994).

The pattern of expression of LXRs and their oxysterol ligands first suggested that these receptors may have a role in cholesterol metabolism. Cholesterol has two essential metabolic fates in mammals: conversion into steroid hormones or bile acids. Since steroid hormone synthesis is known to be governed by the orphan nuclear receptor steroidogenic factor-1 (SF-1) (Parker and Schimmer, 1997), it is possible that LXRs are involved in bile acid synthesis (Janowski et al., 1996). A likely target for any bile acid inducer is cholesterol 7$\alpha$-hydroxylase (Cyp7a), the rate-limiting enzyme in the classical bile acid synthesis pathway (Janowski et al., 1996; Lehmann et at., 1997). Experiments by the inventors and others have shown that the Cyp7a promoter contains a functional LXR response element that can be activated by RXR/LXR heterodimers in an oxysterol- and retinoid-dependent manner (Lehmann et (al., 1997). The formation of bile acids is one of two major pathways for the catabolism and excretion of cholesterol in mammals (Russell and Setchell, 1992). Perturbations in this pathway may lead to a variety of disorders, including cholesterol gallstones, atherosclerosis, and some lipid storage diseases (Akiyoshi et al., 1986; Turley and Dietschy, 1988; Carey and Duane, 1994). Together, these observations have raised an interesting possibility that LXRs may function as transcriptional control points in bile acid metabolism.

The RXR protein of RXR homo- and heterodimers has been observed to be regulated by 9-cis retinoic acid, which binds to the carboxy-teminus of RXR (Mangelsdorf and Evans, 1995). RXR can form heterodimers with numerous other proteins in the nuclear receptor superfamily, including LXR. Depending on the receptor protein that dimerizes with RXR, and the ligands present, the resulting effects of the heterodimer on transcription can vary. Synthetic retinoids have been found to selectively bind and activate RXRs (U.S. Pat. No. 5,780,676 and U.S. Pat. No. 5,455,265).

The potential to modulate lipid concentrations in vivo, by targeting proteins of the nuclear hormone receptor superfamily with specific ligands would be particularly useful in the treatment of various diseases related to lipid metabolism. For example, high blood cholesterol levels are associated with coronary disease. Lowering dietary cholesterol intake can significantly reduce cholesterol levels in most people. However, lowering dietary intake of cholesterol often is not enough, as certain individuals sustain high cholesterol blood levels due to inefficient endogenous cholesterol homeostasis. Thus, the ability to reduce blood cholesterol levels would prove to be extremely beneficial to these individuals. Currently, there are various drugs that are administered to treat hypercholesterolemia and other abnormal blood lipid levels. For example, cholestyramine and colestipol are resins that bind bile acids in the intestinal tract, causing the liver to increase its production of bile acids and thus lower the cholesterol levels, by converting cholesterol into bile acid. However, the efficacy of these drugs is low, they are unpleasant to take, and result in constipation and bloating. Nicotinic acid, gemfibrizol, probucol, and lovastatin also are drugs used to lower blood lipid levels, but each has undesirable side effects associated with it. For example, probucol lowers total cholesterol levels, but also results in the undesirable lowering of HDL cholesterol.

Given the high incidence of coronary artery disease in the United States and its association with high cholesterol, there is a high demand for a treatment that can lower cholesterol levels without adverse side effects. Furthermore, a treatment that can lower LDL cholesterol levels, without affecting total lipid levels is highly desirable.

SUMMARY OF THE INVENTION

It is, therefore, a goal of the present invention, to provide both compositions and methods that are related to cholesterol metabolism and abnormalities therein. More particularly, the invention is intended to provide tool for the identification of compositions for use in treating cholesterol-related pathologies, as well as therapeutic methods of use.

Thus, in a first embodiment, the present invention provides a non-human transgenic mammal, the cells of which comprise at least one non-functional endogenous LXRα allele. The transgenic mammal may further comprise two non-functional endogenous LXRα alleles. The mammal of the present invention may a mouse, rat, hamster, guinea pig, rabbit, cow, and sheep, or other suitable organism.

In particular embodiments, either one or both non-functional LXRα allele may contain (a) an interruption in the LXRα coding sequence, (b) a nonsense mutation in the LXRα coding sequence or (c) a deletion of LXRα coding sequence. Alternatively, the non-functional LXRα allele may result from an alteration in the regulatory region of the LXRα gene. In a particular embodiment, substitution of the endogenous an inducible/repressable promoter for the endogenous LXRα promoter may be utilized. Cells of the transgenic mammal may further comprise an exogenous selectable marker gene under the control of a promoter active in at least one mammalian cell type.

Another aspect of the present invention provides a method for screening an RXR agonist or LXRα agonist candidate substance for the ability to increase bile acid synthesis comprising: 1) providing a cell, 2) contacting the cell with the candidate substance; and 3) monitoring a bile acid-related phenotype of the cell, wherein an increase in the bile acid-related phenotype in the cell treated with the candidate substance, as compared to a similar cell not treated with the candidate substance, indicates that the candidate substance increases bile acid synthesis. In one embodiment of the present invention the cell is a liver cell. The bile acid-related phenotype may be expression of a gene involved in bile acid synthesis, for example, Cyp7a. The candidate substance may be an RXR agonist, more particularly a rexinoid.

Also contemplated in the present invention is a method for screening a candidate substance for the ability to reduce cholesterol levels in a mammal comprising: 1) providing a non-human transgenic mammal, the cells of which comprise at least one non-functional endogenous LXRα allele; 2) treating the mammal with the candidate substance; and 3) monitoring a cholesterol-related phenotype in the mammal, wherein a reduction in the cholesterol-related phenotype in mammals treated with the candidate substance, as compared to a similar mammal not treated with the candidate substance, indicates that the candidate substance reduces cholesterol levels. The mammal may be selected from the group consisting of mouse, rat, hamster, guinea pig, rabbit, cow, and sheep. The cells of the mammal may comprise two non-functional endogenous LXRα alleles.

The phenotype may be cholesterol absorption, circulating cholesterol, hepatic cholesterol, hepatomegaly, atherosclerosis, cardiac failure, cardiac (atrophy/hypertrophy), activity level, survival, cancer, reproduction, immune function, skin disease, cognitive function, and adrenal function. The mammal may be maintained on a high cholesterol diet. The mammal may further be treated with an agent that blocks cholesterol biosynthesis.

Also contemplated is a method for screening a candidate substance for the ability to increase bile acid synthesis in a mammal comprising: 1) providing a non-human transgenic mammal, the cells of which comprise at least one non-functional endogenous LXRα allele; 2) treating the mammal with the candidate substance; and 3) monitoring a bile acid-related phenotype in said mammal wherein an increase in the bile acid-related phenotype in mammals treated with the candidate substance, as compared to a similar mammal not treated with the candidate substance, indicates that the candidate substance increases bile acid synthesis. The mammal may be selected from the group consisting of mouse; rat, hamster, guinea pig, rabbit, cow, and sheep. The bile acid-related phenotype may be selected from the group consisting of cholesterol level, Cyp7a synthesis, fecal bile acid excretion, bile acid pool size and bile acid composition.

Another aspect of the present invention is a method for screening a rexinoid for the ability to inhibit cholesterol absorption by an intestinal cell comprising: 1) providing an intestinal cell; 2) treating the cell with the rexinoid; and 3) monitoring cholesterol absorption by the cell, wherein a reduction in cholesterol absorption by the cell treated with the rexinoid, as compared to a similar cell not treated with the rexinoid, indicates that the rexinoid is an inhibitor of cholesterol absorption. The cell may be a duodenal cell, optionally located in a mammal. The method may further comprise comparing the effect of the candidate substance on cholesterol absorption on a cell comprising one or two non-functional endogenous LXRα alleles.

Another aspect of the present invention is a method of reducing cholesterol levels in a mammal comprising the step of treating the mammal with an RXR agonist. The agonist may be a rexinoid. The method may further comprise treating the mammal with an agent that inhibits cholesterol biosynthesis, for example, an HMG CoA reductase inhibitor. The mammal may be a human. The method may further comprise stimulating bile acid synthesis in the mammal or reducing cholesterol intake by the mammal.

In yet another aspect of the present invention, there is provide a method for inhibiting cholesterol absorption in a mammal comprising treating the mammal with an RXR agonist. The agonist may be a rexinoid and the mammal may be human The present invention further contemplates a transgenic cell which comprises at least one non-functional endogenous LXRα allele. Additionally, the transgenic cell may comprises two non-functional endogenous LXRα alleles.

Also contemplated is a rexinoid compound that inhibits cholesterol absorption, identified by a process comprising: 1) providing an intestinal cell; 2) treating the cell with a rexinoid; and 3) monitoring cholesterol absorption by the cell, wherein a reduction in cholesterol absorption by the cell treated with the rexinoid, as compared to a similar cell not treated with the rexinoid, identified the rexinoid as an inhibitor of cholesterol absorption.

Additionally, the present invention provides a rexinoid compound that inhibits cholesterol absorption, produced by a process comprising: 1) providing an intestinal cell; 2) treating the cell with a rexinoid; 3) monitoring cholesterol absorption by the cell, wherein a reduction in cholesterol absorption by the cell treated with said rexinoid, as compared to a similar cell not treated with a rexinoid, identified the rexinoid as an inhibitor of cholesterol absorption; and 4) producing said rexinoid compound.

The present invention also provides a method of screening for a modulator of ABC1 expression comprising: 1) providing a cell expressing an RXR; 2) contacting said cell with a rexinoid and a candidate substance; and 3) determining the expression of ABC1 in said cell, wherein a change in expression of ABC1, as compared to a cell of step (b), indicates that said candidate substance is a modulator of ABC1 expression. Screening for a modulator of ABC1 expression further comprises the step of determining the expression of ABC1 in a cell expressing RXR in the absence of said candidate substance. ABC1 expression is measured by RNA analysis, such as Northern analysis or PCR. Alternatively, ABC1 expression is measured by protein analysis, such as ELISA or Western blot. In preferred embodiments, screening for a modulator of ABC1 expression in a cell comprises an exogenous marker cassette comprising a polynucleotide encoding a screenable marker operably linked to an ABC1 promoter region. In preferred embodiments, the screenable marker is an esterase, phosphatase, protease, green flourescent protein, luciferase, chloramphenicol acetyl transferase, β-galactosidase. β-glucuronidase or a drug resistance marker. Preferred cells for screening for a modulator of ABC1 expression are cells expressing an RXR such as intestinal cells, preferably of duodenal or jejunal origin. Screening for a modulator of ABC1 expression may be done in vivo.

The present invention also provides for a method of making a modulator of ABC1 expression comprising: 1) providing a cell expressing an RXR; 2) contacting said cell with a rexinoid and a candidate substance; 3) determining the expression of ABC1 in said cell, wherein a change in expression of ABC1, as compared to a cell of step (b), indicates that said candidate substance is a modulator of ABC1 expression; and 4) making said modulator.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
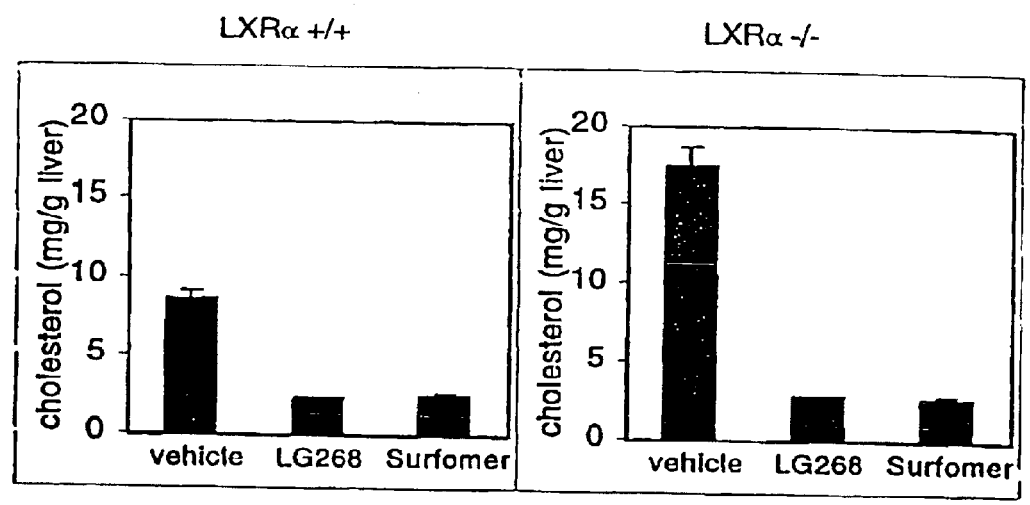
FIG. 1—Liver Accumulation of Cholesterol in LXRα Wild-Type and Knock-Out Mice Treated with LG268. Values represent mean ±SEM for 6 animals per group. LG268 given at 30 mg/kg body weight for 10 days.
Figure 2A:
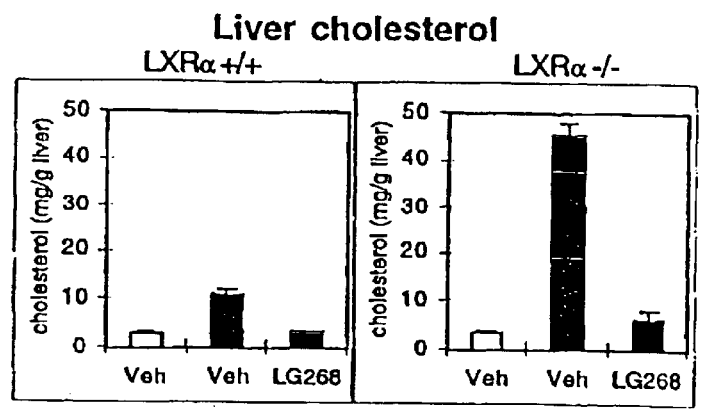
FIG. 2A and FIG. 2B—Comparison of Liver Cholesterol Levels with Bile Acid Production in LXRα Wild-Type and Knock-Out Mice Treated with LG268. Open bars represent mice fed control diet; closed bars represent mice fed diet containing 2% cholesterol. Values represent mean ±SEM for 6 mice per group. LG268 given at 30 mg/kg body weight for 7 days. Veh=Vehicle alone.
Figure 2B:
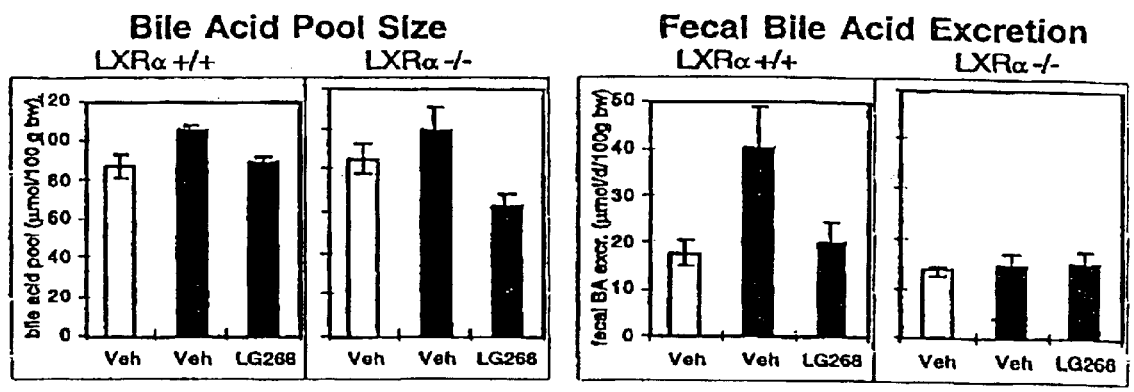
Figure 3:
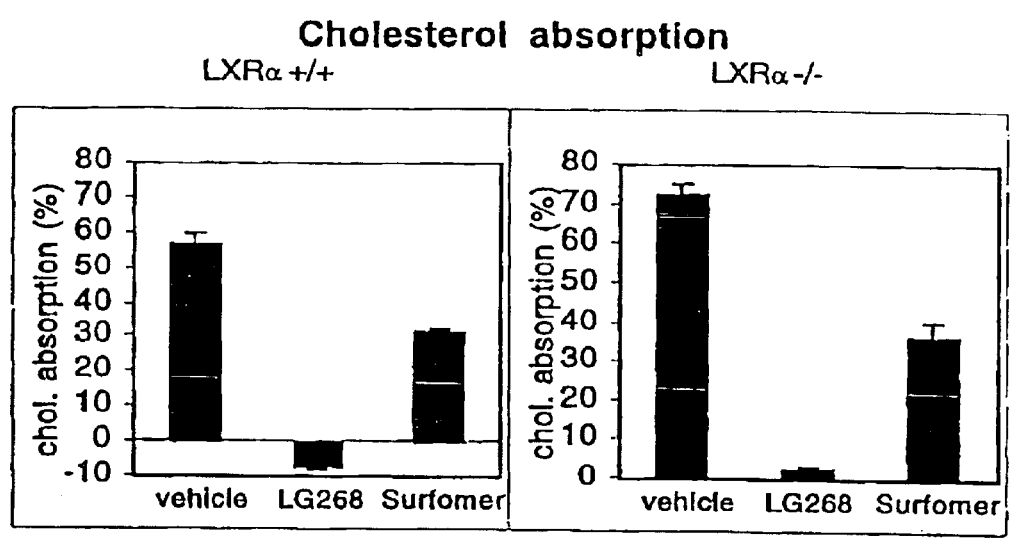
FIG. 3—Cholesterol Absorption in LXRα Wild-Type and Knock-Out Mice Treated with LG268. Values represent mean ±SEM for 6 mice per group. LG268 given at 30 mg/kg body weight for 10 days.

Although cholesterol is an essential molecule required for the structural integrity of cell membranes, as a precursor for steroid hormones and bile acids, high levels of blood cholesterol can be detrimental. Hypercholesterolemia has been implicated in coronary artery disease (i.e., atherosclerosis, heart attack, and stroke) (Schultheis, 1990; Mitchell, 1990). Coronary artery disease is the leading cause of death in the United States, accounting for approximately 600,000 deaths per year. Thus, the need exists for methods of treatment that can reduce cholesterol levels and methods to screen patients at risk for high cholesterol.

The present invention seeks to ameliorate high blood cholesterol levels by stimulating the RXR/LXRα hormone receptor. Rexinoids have been shown to bind to the RXR receptor, but not in any cholesterol-regulatory fashion. However, LXRα does have a putative relationship to cholesterol metabolism through bile acid metabolism. Since LXRα functions as a heterodimer with the retinoid X receptor (RXR, Willy et al., 1995) the inventors sought to determine if RXR agonists (rexinoids) also could affect cholesterol metabolism.

Initial experiments utilized the RXR-specific ligand, LG100268 (hereafter referred to as LG268), which binds and activates all RXR subtypes and fails to exhibit binding to other related nuclear receptors (Boehm, 1995). Studies were performed in wild-type and LXRα-knockout mouse strains and in Syrian golden hamsters. LG268 produced dramatic effects on cholesterol homeostasis in mice and hamsters by preventing the liver accumulation of cholesterol typically seen in cholesterol-fed animals. This effect did not involve LXRα, since it was observed in the LXRα knockout mouse strain, nor did it occur by modulation of bile acid biosynthesis to eliminate ingested cholesterol, since the homozygote knockout could not bile acid synthesis. Rather, LG268 inhibited the intestinal absorption of cholesterol in a specific, dose-dependent manner with remarkable potency (effective at a dose of 1.4 mg/kg body weight which is equivalent to 0.0015% of the diet in mouse experiments). Absorption of other lipids appeared to be unaffected. As further evidence for the efficacy of rexinoids in blocking cholesterol absorption, even when mice were fed a diet containing 0.2% cholesterol (ten times what their basal diet provides), LG268 effected a total block in cholesterol absorption and the treated mice exhibited dramatically increased tissue cholesterol synthesis rates in order to meet their cholesterol needs.

Thus, LG268 and rexinoids provide powerful tools to elucidate the mechanism of cholesterol absorption and homeostasis. Practical applications include the use of these agents alone, or in conjunction with other anti-hypocholesterolemic agents such as the statins, niacin, or bile acid sequestrants (surfomer) to prevent the elevated blood cholesterol levels associated with atherosclerosis and heart disease.

A. Cholesterol Metabolism

Most cholesterol synthesis in animals takes place in the liver. The 5-carbon isoprene unit is the key intermediate in cholesterol biosynthesis. Cholesterol, is made from acetyl-CoA in four steps (Rao, 1995; Bocan et al., 1998). The first step is the condensation of three acetate units catalyzed by thiolase, HMG-CoA synthase, and HMG-CoA reductase, resulting in the formation of the molecule mevalonate. Second, mevalonate is converted into activated isoprene units through a series of phosphorylation steps. Third, the 5-carbon isoprene units are polymerized into a 30-carbon linear structure of squalene through a series of enzyme catalyzed reactions. Finally, the squalene chain is cyclized into the four rings of the steroid nucleus and through further enzymatic steps of oxidation and demethylation, the final product of cholesterol is formed. Cholesterol can also be catabolized into oxysterols or converted into bile acids or steroid hormones, which is regulated by a cholesterol homeostasis feedback mechanism (Osborne and LaMorte, 1998)

Only a small percentage of the cholesterol synthesized in the liver is incorporated into the membranes of hepatocytes. The majority of the cholesterol made in the liver is exported to other tissues as either bile acids or cholesterol esters. While bile acids and bile salts are relatively hydrophilic cholesterol derivatives, aiding in lipid digestion, cholesterol esters are more hydrophobic and are formed in the liver by the enzyme acyl-CoA-cholesterol acyl transferase (ACAT). ACAT catalyzes the transfer of fatty acids from coenzyme A to the hydroxy group of cholesterol, which converts the cholesterol into a more hydrophobic molecule. Cholesterol esters are stored in the liver or transported to other tissues. The movement of cholesterol and cholesterol esters from the liver to tissues where they will be stored or utilized, require special carrier proteins (apolipoproteins) due to cholesterols relative water insolubility. These apolipoproteins, form aggregates with cholesterol and other lipids such as phospholipids and triacylglycerides, to form the carrier complexes known as plasma lipoproteins.

B. RXR Heterodimers

In has been assumed that receptors such as the TR and RAR, like the steroid receptors, function as homodimers. While the TR homodimer can be formed (Forman et al., 1989; Wahlström et al., 1992), an accessory factor present in nuclear extracts was required for high affinity binding of VDR, TR, and RAR to their cognate HREs (reviewed by Glass, 1994). Shortly after the identification of RXR (Mangelsdorf et al., 1990), a series of studies in several laboratories produced the consensual finding that RXR was the common missing factor (Yu et al., 1991; Kliewer et al., 1992a; 1992b; Leid et al., 1992b; Zhang et al., 1992; Marks et al., 1992; Bugge et al., 1992). There now are known to be three mammalian RXR isoforms, and, remarkably, these are the only proteins that can subserve this function (Mangelsdorf et al., 1992; Leid et al., 1992b). In Drosophila, the RXR homolog Ultraspiracle is a partner for the ecdysone receptor, indicating that heterodimerization evolved prior to the divergence of vertebrates and invertebrates.

Because DRs are asymmetric, heterodimer complexes should bind these elements in an asymmetric fashion. Indeed, it now has been established that on DR3, DR4, and DR5, RXR occupies the 5' half-site and the partner (e.g., VDR, TR, and RAR, respectively) occupies the 3' half-site (Perlmann et al., 1993; Kurokawa et al., 1993; Zechel et al., 1994). On DR1, RXR can bind as both a homodimer and as a heterodimer with RAR. Interestingly, the polarity of the RXR/RAR heterodimer on DR1 is reversed (Kurokawa et al., 1994). In many cell types, the consequence of this reverse polarity binding is that the RAR/RXR heterodimer is a potent repressor of the ligand-activated RXR homodimer (Mangelsdorf et al., 1991; Kurokawa et al., 1995).

Unexpectedly, the ligand-induced transcription activities for RXR are suppressed when complexed with VDR, TR, and RAR. In RXR/TR and RXR/RAR, the formation of the heterodimer actually prevents the RXR from binding its ligand (Kurokawa et al., 1994; Forman et al., 1995c). The restriction of RXR ligand binding within several of these heterodimers indicates that 9-cis retinoic acid responsiveness is not an obligatory consequence of heterodimerization with RXR. Thus, in these instances, RXR is said to be a silent partner. Nonetheless, there are several examples in which RXR can be an active partner (reviewed by Leblanc and Stunnenberg, 1995). One example occurs in the PPAR/RXR heterodimer, in which both receptors are independently responsive and are synergistically activated in the presence of both ligands (Kliewer et al., 1992b). Similarly, heterodimeric complexes of RXR with the orphan receptor LXR or farnesoid X receptor (FXR) also retain 9-cis retinoic acid responsiveness, further supporting the view that RXR can either be a silent partner or a hormone responsive partner (Willy et al., 1995; Forman et al., 1995a). The final and perhaps most unusual example of RXR responsiveness occurs in the complex formed with the orphan receptor NGFI-B (Perlmann and Jansson, 1995; Forman et al., 1995c). This receptor has been shown to contribute to T cell apoptosis and is capable of binding to target DNA as a monomer. However, in the presence of RXR, it forms a stable heterodimer that is 9-cis retinoic acid responsive. Thus, RXR is a critical component of heterodimer formation, which in turn is critical to generating diversity of hormone responses.

C. ABC Transporter and ABC-1 Gene

The ATP-binding cassette (ABC) transporters, also called the "traffic ATPases", comprise a superfamily of membrane proteins that mediate transport and channel functions in prokaryotes and eukaryotes (Higgins, 1992). ABC proteins share a similar overall structure and significant sequence homology. All ABC proteins contain a conserved domain of approximately two hundred amino acid residues which includes one or more nucleotide binding domains. A majority of these proteins are involved in active transport of molecules across membranes. Eukaryotic ABC proteins include: β-glycoproteins, also known as multidrug resistance (MDR) proteins, which are associated with resistance to a wide range of hydrophobic drugs (MDR1; Gottesman, Pastan, 1993) or with phosphatidylcholine transport (MDR2; Ruetz, Gros, 1994); CFTR, the cystic fibrosis transmembrane conductance regulator (Welsh, Smith, 1993); TAP proteins, the transporters associated with antigen processing in mammalian cells (Androlewicz et al., 1994); cMOAT/cMRP1, which is associated with transport of glutathione, glucuronide, and sulfate conjugates across the canalicular membrane (Buchler et al., 1996); and STE6, which exports the a-factor mating pheromone of *S. cerevisiae* (Michaelis, 1993). Prokaryotic ABC proteins include periplasmic nutrient permeases, such as those responsible for uptake of maltose (MalFGK) and histidine (HisMPQ) in gram-negative bacteria, and toxin exporters such as those required for export of hemolysin (HlyB) and colicin (ColV) from *E. coli* (Higgins, 1992).

Savary et al. (1997) recently identified a novel ABC transporter, denoted ABC7, in mouse. The predicted 629 amino acid mouse ABC7 translation product contains six putative transmembrane domains near the N-terminus, followed by an ATP-binding cassette domain. Savary et al. (1997) also disclosed a partial protein sequence from human similar to the C-terminal 340 amino acids of mouse ABC7 protein. Savary et al. reported that the human ABC7 was widely expressed in cell lines, heart, skeletal muscle, pancreas, lung, liver, and placenta. Human ABC7 expression was not -detected in brain.

Mutations in other ABC family members cause a variety of genetic disorders, such as cystic fibrosis, intrahepatic cholestasis, macular degeneration, peroxisomal dysfunction, and immunodeficiency syndromes (Higgins, 1992). The first clue that ABC1 participated in lipid metabolism came with the observation by Schmitz and colleagues that ABC1 expression rose when the cholesterol content of macrophages was increased (Langmann et al., 1999). In an independent study using expression microarrays, Lawn et al. identified the ABC1 mRNA as an upregulated transcript in cholesterol-loaded macrophages (Lawn et al., 1999). Macrophages routinely ingest large amounts of cholesterol in the form of cellular membrane debris and aggregated lipoproteins, and lack the ability to downregulate cholesterol uptake in response to cholesterol loading (Brown and Goldstein, 1983). Consequently, macrophages are heavily dependent on cholesterol efflux (predominantly through transfer to HDL) to prevent accumulation of lipids. Thus, it might be anticipated that proteins that participate in cholesterol efflux, such as ABC1, would be increased in cholesterol-laden macrophages. The current finding of Lawn et al. that ABC1 is located on the cell surface suggests that this transporter may actually physically participate in the hand-off of cholesterol from cells to plasma HDL (Lawn et al., 199). A direct role for ABC-1 in cholesterol homostasis came recently when 3 groups identified the underlying molecular defect of Tangier disease to be mutations in the ABC1 gene (Bodzioch et al., 1999; Rust et al., 1999; Brooks Wilson et al., 1999). Lawn et al. extends these findings and provides a further functional characterization of the ABC1 transporter (Lawn et al., 1999). These findings dovetails nicely with the previous observation that Tangier fibroblasts have a greatly reduced capacity to donate cellular cholesterol (and phospholipids) to apo A-I, the major apolipoprotein of HDL (Francis et al., 1995). The full complement of substrates transported by ABC1 has not been identified, and it is possible that some of the variability in the clinical manifestations of this disease is due to mutation-specific differences in substrate specificity.

D. Transgenic Animals and Cells

Animal models serve as useful vehicles for screening of compounds, for example, for effects on cholesterol levels, cholesterol absorption, and bile acid synthesis. Transgenic animals, defined as animals with engineered genomes, may prove particularly useful in certain applications. In the present application, the focus is on regulation of cholesterol metabolism and the role of LXRα in this process. Thus, transgenic mice were produced that lacked either one, or both, of the endogenous LXRα alleles. Animals lacking one or both alleles showed increases in cholesterol levels, enlarged livers and reduced bile acid secretion. These animals have proved useful not only in elucidating the biology of this signalling pathway, but as tools in examining possible therapeutic compositions and methods of treatment.

Transgenic non-human animals of the present invention will have at least one non-functional endogenous LXRα allele. It further is contemplated that the transgenic non-human animal of the present invention may have both LXRα alleles altered, thus providing cells which lack functional LXRα. The non-functional LXRα allele(s) can contain an interruption of the LXRα coding sequence, a nonsense mutation that truncates the LXRα product, a deletion of the LXRα coding sequence or alterations in the LXRα regulatory region. In designing a heterologous gene for expression in animals, sequences which interfere with the efficacy of gene expression, such as coding sequences, promoters, introns, polyadenylation signals, polymerase n termination sequences, hairpins, consensus splice sites and the like, may be eliminated.

Current advances in transgenic approaches and techniques have permitted the manipulation of a variety of animal genomes via gene addition, gene deletion, or gene modifications (Franz et al., 1997). For example, mosquitos (Fallon, 1996), trout (Ono et al., 1997), zebrafish (Caldovic and Hackett, 1995), pigs (Van Cott et al., 1997) and cows (Haskell and Bowen, 1995), are just a few of the many animals being studied by transgenics. The creation of transgenic animals that express human proteins such as α-1-antitrypsin, in sheep (Carver et al., 1993); decay accelerating factor, in pigs (Cozzi et al., 1997); and plasminogen activator, in goats (Ebert et al., 1991) have previously been demonstrated. The transgenic synthesis of human hemoglobin (U.S. Pat. No. 5,602,306, specifcally incorporated herein by reference) and fibrinogen (U.S. Pat. No. 5,639,940, specifcally incorporated herein by reference) in non-human animals have also been disclosed, each specifically incorporated herein by reference in its entirety. Further, transgenic mice and rat models have recently been described as new directions to study and treat cardiovascular diseases such as hypertension in humans (Franz et al., 1997; Pinto-Siestma and Paul, 1997). The construction of a transgenic mouse model has recently been used to assay potential treatments for Alzheimer's disease (U.S. Pat. No. 5,720,936, specifically incorporated herein by reference in its entirety). It is contemplated in the present invention that transgenic animals contribute valuable information as models for studying the effects of ligands specific for the RXR nuclear hormone receptor in transgenic LXRα knockout animal models.

I. Selection and Screening

The present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fludrometric, radioisotopic or spectropllotometric analysis of the cell culture.

Exemplary enzymes include esterases, phosphatases, proteases (tissue plasminogen activator or urokinase) and other enzymes capable of being detected by their activity, as will be known to those skilled in the art. More preferred for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells. As the previously existing selection procedures for identifying correctly modified cells required culture of the manipulated cells for 10–14 days in a chemical known as G418, it was necessary to pass the cells to fresh feeders during the selection procedure. However, the use of the green fluorescent protein (GFP) as an identification marker allows for identification of transgenic colonies without the need for passage or addition of selectable media. As a results the cells remain healthier and, since are not passaged repeatedly, maintain their ability to generate a living offspring after nuclear transfer or blastocyst injection.

Other preferred examples are the enzyme chloramphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

The enzyme luciferase is useful as a screenable marker in the context of the present invention (Kang et al., 1998). In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. The above techniques also could be utilized if the screenable marker is the green fluorescent protein.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. Therefore it is proposed that combinations of selection and screening will enable one to identify transformants in a wider variety of cell and tissue types.

II. Characterization

To confirm the presence of the exogenous DNA or "transgene(s)" in the transformed cells, a variety of assays may be performed. Such assays include, for example, "molecular biological" assays, such as Southern and Northern blotting, RT-PCR™ and PCR™; "biochemical" assays, such as detecting the presence of a protein product, e.g., by immunological means (ELISAs and Western blots) or by enzymatic function assay.

III. Gene Expression

While Southern blotting and PCR™ may be used to detect the LXRα gene(s) in question, they do not provide information as to whether the gene is being expressed. Expression may be evaluated by RT-PCR™ for mRNA and/or specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Transgenic animals are described that synthesize epitope tagged prion proteins as a method of detecting the expressed protein(s) (U.S. Pat. No. 5,789,655, specifically incorporated herein by reference in its entirety). Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the cells of the animal or human.

IV. DNA Integration, RNA Expression and Inheritance

Genomic DNA may be isolated from animal cell lines or any animal parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transfornant, but does not prove integration of the introduced gene into the host cell genome. It is the experience of the inventors, however, that DNA has been integrated into the genome of all transformants that demonstrate the presence of the gene through PCR™ analysis (Wu et al., 1998). In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™ e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Whereas DNA analysis techniques may be conducted using DNA isolated from any part of an animal, RNA will only be expressed in particular cells or tissue types and hence it will be necessary to prepare RNA for analysis from these tissues. PCR™ techniques may also be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

V. Methods of Transformation a. Electroporation

In certain preferred embodiments of the present invention, the transgenic construct is introduced into the primordial germ cells via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloraniphenicol acetyltransferase gene (Tur-Kaspa et al., 1986) in this manner.

It is contemplated that electroporation conditions for primordial germ cells from different sources may be optimized. One may particularly with to optimize such parameters as the voltage, the capacitance, the time and the electroporation media composition. The execution of other routine adjustments will be known to those of skill in the art.

b. Particle Bombardment

One of the preferred embodiments of the invention for transferring a naked DNA construct into cells involves particle bombardment. This method depends on the ability to accelerate DNA-coated microprojectiles to a high velocity allowing them to pierce cell membranes and enter cells without killing them (Klein et al., 1987). The microprojectiles used have consisted of biologically inert substances such as tungsten, platinum or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of primordial germ cells.

Accordingly, it is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

c. Calcium Phosphate Co-Precipitation or DEAE-Dextran Treatment

In other preferred embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

d. Direct Microinjection or Sonication Loading

Further embodiments of the present invention include the introduction of the transgenic construct by direct microinjection or sonication loading. Direct microinjection has been used to introduce nucleic acid constructs into Xenopus oocytes (Harland and Weintraub, 1985), and LTK fibroblasts have been transfected with the thymidine kinase gene by sonication loading (Fechheimer et al., 1987).

e. Liposome Mediated Transformation

In a further embodiment of the invention, the transgenic construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a transgenic construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et (L (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

f. Viral Transformation i) Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a transgene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et at., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

ii) Adenoviral Infection

One method for delivery of the transgenic constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a transgenic construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by AdS DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoletic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

iii) AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

iv) Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

g. Adenoviral Assisted Transfection

In certain embodiments of the present invention, the transgenic construct is introduced into the cell using adenovirus assisted transfection. Increased transfection efficiencies have been reported in cell systems using adenovirus coupled systems (Kelleher and Vos, 1994; Cotten et al., 1992; Curiel, 1994), and the inventors contemplate using the same technique to increase transfection efficiencies.

h. Receptor Mediated Transfection

Still further constructs that may be employed to deliver the transgenic construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds a degree of specificity to the present invention. Specific delivery in the context of another mammalian cell type is described by Wu and Wu (1993; incorporated herein by reference).

Certain transgenic delivery constructs comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Ferkol et al., 1993; Perales et al., 1994; Myers, EPO 0273085), which establishes the operability of the technique.

In other embodiments, the DNA delivery vehicle component may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the delivery vehicles may be a liposome itself, which will preferably comprise one or more lipids or glycoproteins that direct cell-specific binding. For example, Nicolau et al. (1987) employed lactosyl-ceramide, a galactose-terminal asialoganglioside, incorporated into liposomes and observed an increase in the uptake of the insulin gene by hepatocytes. It is contemplated that the transgenic constructs of the present invention can be specifically delivered into the target cells in a similar manner.

VI. Vectors and Regularity Signals

Vectors of the present invention are designed, primarily, to produce non-functional alleles in LXRα. As described above in the section dealing with transgenic animals, creation of non-functional alleles can result from a variety of different genetic changes. These include interruption of the gene, deletion of the gene, introduction of a stop codon, or alteration of a regulatory signal. Other methods include alteration of a splice site or some signal required for other post-transcriptional or post-translational processing.

In many instances, the vectors of the present invention do not encode a functional LXRα gene and, thus, need not contain a promoter driving that gene. However, it may prove useful to provide functional LXRα genes with regulatable promoters (i.e., inducible, repressable, tissue specific). Also, the vectors usually will contain a selectable marker if, for no other reason, to facilitate their production in vitro. However, selectable markers may play an important role in producing transgenic cells and animals. Thus, a discussion of promoters is useful here.

TABLE 1

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids poly(rI)X poly(rc) | Huang et al., 1981; Lee et al., 1981; Majors and Varmus, 1983; Chandler et al., 1983; Lee et al., 1984; Fonta et al., 1985; Sakai et al., 1986 |
| β-Interferon | | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

TABLE 2

Other Promoter/Enhancer Elements

| Promoter/Enhancer | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-Antirypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian. 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |

TABLE 2-continued

Other Promoter/Enhancer Elements

| Promoter/Enhancer | References |
|---|---|
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immuno-deficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

Another signal that may prove useful are polyadenylation signals (hGH, BGH, SV40).

In certain embodiments of the invention, the use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

As discussed above, in certain embodiments of the invention, a cell may be identified and selected in vitro or in vivo by including a marker in the expression construct. Such markers confer an identifiable change to the cell permitting easy identification of cells containing the expression construct. Usually, the inclusion of a drug selection marker aids in cloning and in the selection of transformants, for example, genes that confer resistance to neomycin, puromycin, hygromycin, DHFR, GPT, zeocin, tetracycline and histidinol are useful selectable markers. Alternatively, enzymes such as herpes simplex virus thymidine kinase (tk) or chloramphenicol acetyltransferase (CAT) may be employed.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In any event, it will be understood that promoters are DNA elements which when positioned functionally upstream of a gene leads to the expression of that gene. Most transgene constructs of the present invention are functionally positioned downstream of a promoter element.

a. Promoters Specific for Undifferentiated Cells

Preferred for use in the present invention are promoters which are active in undifferentiated cells. Promoters that lead to high levels of expression in undifferentiated cells include the phosphoglycerate kinase (pgk) promoter and the octamer binding transcription factor 4 (Oct-4) promoter. The pgk promoter is known to lead to high levels of expression in undifferentiated mouse ES cells.

Transgenic experiments have identified a regulatory region upstream of the Oct-4 gene that is capable of targeting high level expression to the undifferentiated inner cell mass and the primordial germ cells (Yeom et al., 1996). By using the Oct-4 promoter, expression would be limited to highly undifferentiated cells and PGCs, thereby allowing for selection of the cells with the highest probability of contributing to the germ line by measurement of the expression levels of a selected marker protein, preferably green fluorescent protein. Use of the Oct-4 promoter also allows for early screening of putative transgenic animals, saving considerable time and expense, by not requiring that chimeras be saved until breeding age for testing, and by not requiring expensive and prolonged breeding tests.

b. Eukaryotic and Viral Promoters and Enhancers

Preferred for use in the present invention is the cytomegalovirus (CMV) promoter. This promoter is commercially available from Invitrogen in the vector pcDNAIII, which is preferred for use in the present invention. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

E. Screening Assays

The present invention provides methods of screening compounds for a variety of different activities using a number different assay formats. The assays, at their most basic level, assess the impact that a given candidate substance will have upon a cell, tissue, organ or organism, as compared to that same cell, tissue organ or organism in the absence of the candidate substance. In certain embodiments, using genetically related but distinct cells, it is possible to ascertain some information about how the candidate substance is affecting the target.

In some instances, for example, where cholesterol levels or adsorption are to be measured, it may prove useful to use a system where there is increased cholesterol introduced into the test system, be that system a cell, a cell culture, a tissue, and organ or an organism. Such "high cholesterol" media or diets are well known to those of skill in the art. As an example, a 2% cholesterol diet is utilized for testing in mice and designated "high cholesterol" for the purposes of this study.

As used herein, the term "candidate substance" refers to any molecule. The candidate substance may be a classic pharmaceutical, a peptide, a protein or fragment thereof, a synthetic small molecule, or an oligo- or polynucleotide or a lipid. The active compounds also include naturally-occurring substances, fragments or parts thereof, for example, compounds isolated from natural sources, such as animals, bacteria, fungi, plant sources, including leaves and bark, and marine samples. Also included are active combinations of known compounds which are inactive or suboptimally active when administered separately.

It may prove to be the case that the most useful compounds for identification through application of a screening assay will be compounds that are structurally related to known compounds that are found to have desired activities. So-called "rational drug design," which is based on the structural or physical attributes of a given candidate substance and its similarity or difference with respect to functional and non-functional substances, permits a directed method of modification towards the goal of improving or optimizing function. Where a particular molecular target is known, rational drug design may also take into account one or more structural or physical attributes of the target when designing or modifying the candidate substances.

Screening assays are relatively simple to set up and perform. Thus, in assaying for a candidate substance, one must provide a suitable system in which to test the substance. Typically, the system is a cell or cell culture, or an organism. One then either contacts the candidate substance with the cell, or administers the candidate substance to the organism. One then measures some read out of cellular, tissue, organ or organismal function or characteristic to ascertain the effect of the candidate substance. Of course, this read out takes into account, or actually measures, the cellular, tissue, organ or organismal function or characteristic in an untreated cell, tissue, organ or organism.

It also must be recognized that some substances may not prove to have an effect at lower dosages ranges. Therefore, it may prove useful to conduct dose response experiments, especially when there is no related compound upon which to base an estimate of the effective amount. However, solubility and toxicity considerations usually are available to provide a reasonable upper limit upon the amount of a substance that will be tested.

Two particular classes of compounds will hold particular significance in the following methods—RXR agonists and LXRα agonists. As discussed above, these two molecules form a heterodimer which is an important receptor for regulating, among other things, bile acid synthesis. The natural agonist of RXR is 9-cis retinoic acid. One particular class of RXR agonists is the rexinoids, synthetic analogs of retinoic acids. Various rexinoids are described in U.S. Pat. Nos. 5,780,676 and 5,455,265, which are incorporated by reference. The present inventors have shown that some, but not all, rexinoid agonists of RXR are capable of decreasing cholesterol uptake.

The other class of compounds that will be of particular interest are agonists of LXRα. The natural agonists for LXRα are oxycholesterols, oxygenated metabolic derivatives of cholesterol. Selected analogs of these compounds should prove particularly useful in increasing bile acid synthesis.

As discussed below, there are a variety of different assays, and hence, a variety of different read outs for "activity." The examples provided below should not be considered limiting and are merely exemplary. The skilled artisan is well aware of other examples of read outs depending on the nature of the assay and the intent of the screen. It will, of course, be understood that all the screening methods of the present invention are useful in themselves notwithstanding the fact that effective candidates may not be found. The invention provides methods for screening for such candidates, not solely methods of finding them.

Also, while the specific embodiments described below focus on in vitro and in vivo examples, the present inventors also contemplate ex vivo experiments using whole tissues or organs derived from suitable research animals, human tissue donors or cadavers.

I. Method for Screening for Increase in Bile Acid Synthesis a. In vitro

Bile acids are an important tool in metabolizing cholesterol and, thus, may provide one mechanism by which abnormally high cholesterol levels may be countered in vivo Therefore, one screening assay will focus on the ability of candidate substances to increase bile acid synthesis. This method generally includes the steps of:

(a) providing a cell;

(b) contacting said cell with said candidate substance; and (c) monitoring a bile acid-related phenotype, as compared to a similar cell not treated with said candidate substance.

If there is an increase in the bile acid-related phenotype in the treated, as compared to the untreated cell, the candidate substance is identified as having the ability to increase bile acid synthesis. In this particular embodiment, the compounds to be tested are RXR and LXRα agonists. With respect to the former, one particular group of interest are the rexinoid compounds (see above).

The cell of interest should contain RXR/LXRα receptors in sufficient amounts to effect a measurable change in the phenotype of the cell. Cells particularly suited to this purpose are liver cells, and may be subjected to a high cholesterol environment. Use of primary hepatocytes is a preferred embodiment. One may measure any bile-acid related phenotype, but a particular phenotype is the induction of cholesterol 7α-hydroxylase (Cyp7a) expression. This gene is the rate limiting enzyme in bile acid synthesis.

Though a normal cell can be utilized in this assay, the ability to discern the bile acid induced versus uninduced states of such cells may be difficult. For example, in a normal cholesterol environment, there will be little stimulation of bile acid production. Induction with a candidate substance may, in and of itself, result in a fairly significant increase in bile acid production. Alternatively, the absence of oxycholesterol may handicap the cell such that induction is not possible. In a high cholesterol environment, however, oxycholesterol will be plentiful and bile acid synthesis will be activated. In this case, however, it may be difficult to observe any "superinduction" by the candidate substance.

A convenient compromise between these two situations is where the cell carries only a single functional LXRα allele. In this case, the high cholesterol environment, which should enable induction of bile acid synthesis, will not "max out" bile acid synthesis because only about one-half of the receptor capacity of the cells is being expressed. It is important that these cells still retain one functional LXRα allele, since loss of both alleles would render the cells completely unresponsive to RXR/LXRα agonists. Thus, cells that are genetically altered to be heterozygous for the LXRα allele (+/−) will prove particularly useful.

b. In vivo

As a parallel to the preceding assay, one may wish to examine effects of a candidate substance on bile acid synthesis in vivo. This assay will be similar to the preceding in vitro assay with the following notable exceptions. First, obviously, the candidate substance is provided to an animal rather than a cell or cell culture. Second, the readouts in the assay will include cholesterol levels, Cyp7a synthesis, fecal bile acid excretion, bile acid pool size and bile acid composition. Third, one may wish to screen more than just RXR and LXRα agonists for increases in bile acid synthesis. In this case, one will utilize a heterozygous LXRα (+/−) knockout animal.

II. Method for Screening for Decrease in Cholesterol Absorption a. In vitro

In another embodiment, the present invention provides for the screening of rexinoid compounds for their ability to inhibit adsorption of cholesterol by intestinal cells. A high cholesterol environment can be utilized. The method includes the steps of:

(a) providing an intestinal cell;

(b) contacting said cell with the candidate rexinoid; and (c) monitoring cholesterol absorption by said cell, as compared to a similar cell not treated with said rexinoid.

A decrease in absorption of cholesterol in the treated cell, as compared to the untreated cell, indicates that the rexinoid is an inhibitor of cholesterol absorption. Monitoring of uptake of a labeled (radioactive, chemilluminescent, fluorometric) cholesterol is one method of measuring activity. A particularly preferred target cell is a duodenal cell.

As mentioned briefly, above, it may prove useful to examine the effects of an inhibitor, identified according to this method, on cells comprising one or two non-functional LXRα alleles. By showing the dependence of the inhibitor on the presence of a functional RXR/LXRα, information can be gained about how the inhibitor is effecting a decrease in cholesterol absorption.

It also may prove useful, in both the in vivo and in vitro embodiments, to add another an agent that inhibits cholesterol biosynthesis. Together, these agents may prove to act even better in concert than they do individually. A group of compounds that are used to inhibit cholesterol biosynthesis are HMG CoA reductase inhibitors, the so-called "Statins."

b. In Vivo

Again, it may prove useful to screen for effects of a potential inhibitor of cholesterol absorption in vivo. This assay will be similar to the preceding in vitro assay with the following notable exceptions. First, obviously, the candidate substance is provided to an animal rather than a cell or cell culture. Second, the readouts in the assay will include cholesterol absorption directly, or indirectly by measuring circulating cholesterol levels, hepatic cholesterol, hepatomegaly, atherosclerosis, cardiac failure, cardiac hypertrophy or atrophy, activity level, survival, cancer, reproduction, immune function, skin disease, cognitive function and adrenal function. Particularly preferred will be the assay reported by Turley et al. (1994), which is incorporated by reference. Third, one may wish to screen more than just rexinoids for inhibition of cholesterol absorption. In this case, one will utilize a homozygous heterozygous LXRα (−/−; +/−) knockout animal.

III. Method for Screening for Reduction in In Vivo Cholesterol Levels

In another method, one may wish to look directly at the effects of a compound, or a combination of compounds, on cholesterol levels in vivo. The method includes the steps of:

(a) providing a non-human transgenic mammal, the cells of which comprise at least one non-functional endogenous LXRα allele;

(b) treating said mammal with a candidate substance; and (c) monitoring a cholesterol-related phenotype in said mammal, as compared to a similar mammal not treated with said candidate substance.

A change in the cholesterol phenotype indicative of a decrease in cholesterol levels in the treated cell, as compared to the untreated cell, indicates that the candidate substance is an inhibitor of cholesterol levels. Again, one may wish to use other compounds in combination, be they of known or unknown activity on cholesterol levels, in the same assay. The readouts in the assay will include cholesterol absorption directly, or indirectly by measuring circulating cholesterol levels, hepatic cholesterol, hepatomegaly, atherosclerosis, cardiac failure, cardiac hypertrophy or atrophy, activity level, survival, cancer, reproduction, immune function, skin disease, cognitive function and adrenal function. Preferably, the mammal is subjected to a high cholesterol diet.

One could also screen specifically for an RXR (e.g., rexinoid) or LXR agonist's effect on cholesterol levels using a normal animal. This embodiment would likely contemplate only the use of high cholesterol diet.

IV. Method for Screening for Modulation of ABC1 Expression

In another method, one may wish to look directly at the effects of a compound, or a combination of compounds, on ABC-1 levels in vitro or in vivo. The method includes the steps of screening for a modulator of ABC1 expression comprising:

(a) providing a cell expressing an RXR;

(b) contacting said cell with a rexinoid and a candidate substance;

(c) and determining the expression of ABC1 in said cell, wherein a change in expression of ABC1, as compared to a cell of step (b), indicates that said candidate substance is a modulator of ABC1 expression.

Screening for a modulator of ABC1 expression further comprises the step of determining the expression of ABC1 in a cell expressing RXR in the absence of said candidate substance. ABC1 expression is measured by RNA analysis, such as Northern analysis or PCR. Alternatively, ABC1 expression is measured by protein analysis, such as ELISA or Western blot. In preferred embodiments, screening for a modulator of ABC1 expression in a cell comprises an exogenous marker cassette comprising a polynucleotide encoding a screenable marker operably linked to an ABC1 promoter region. The screenable marker may be an esterase, phosphatase, protease, green flourescent protein, luciferase, chloramphenicol acetyl transferase, β-galactosidase, β-glucuronidase or a drug resistance marker. Preferred cells for screening for a modulator of ABC1 expression are cells expressing an RXR such as intestinal cells, preferably of duodenal or jejunal origin. Screening for a modulator of ABC1 expression may be done in vivo.

The present invention also provides for a method of making a modulator of ABC1 expression comprising: 1) providing a cell expressing an RXR; 2) contacting said cell with a rexinoid and a candidate substance; 3) determining the expression of ABC1 in said cell, wherein a change in expression of ABC1, as compared to a cell of step (b), indicates that said candidate substance is a modulator of ABC1 expression; and 4) making said modulator.

F. Pharmaceutical Compositions and Routes of Delivery

In certain embodiments, the present invention also concerns formulations of one or more agonist compositions for administration to a mammal, that inhibits cholesterol biosynthesis or cholesterol absorption. It will also be understood that, if desired, the agonist compositions disclosed herein may be administered in combination with other agents as well, such as. e.g., various pharmaceutically-active agents. As long as the composition comprises at least one cholesterol inhibitory agonist, there is virtually no limit to other components which may also be included, given that the additional agents do not cause a significant adverse effect upon contact with the target cells or host tissues.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

I. Oral Compositions and Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

II. Injectable Compositions and Delivery

Alternatively, the pharmaceutical compositions disclosed herein may be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

III. Nasal Delivery

The administration of agonist pharmaceutical compositions by intranasal sprays, inhalation, and/or other aerosol delivery vehicles is also considered. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et at., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

IV. Additional Modes of Delivery

In addition to the methods of delivery described above, the following techniques are also contemplated as alternative methods of agonist compound delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208) and feedback controlled delivery (U.S. Pat. No. 5,697,899), each specifically incorporated herein by reference in its entirety.

G. Therapy for Cholesterol Related Disorders

Disorders of lipoprotein metabolism and the susceptibility of human metabolism to adverse effects from diets high is saturated fats have resulted in epidemic atherosclerotic disease in the United States and other developed countries. One aspect of lipid metabolism, and a primary figure in atherosclerotic disease is cholesterol. Lipoproteins transport cholesterol and triglycerides, which are not water soluble, from sites of absorption and synthesis to sites of utilization. Lipoproteins are classified into six major groups based on size, density, electrophoretic mobility and lipid/protein composition. These six classes are chylomicrons (dietary triglycerides), VLDL (endogenous triglycerides), IDL (cholesterol ester, triglycerides), LDL (cholesterol ester), HDL (cholesterol ester), and Lp (cholesterol ester) with the major lipid in each group represented parenthetically. There are both exogenous (dietary) and endogenous (primarily liver) sources of cholesterol. Similarly, there is an exogenous lipid transport pathway to transport dietary cholesterol absorbed in the intestine, and an endogenous pathway to transport cholesterol secreted by the liver.

I. Diseased States

There are several clinical manifestations associated with lipoprotein disorders due to a breakdown somewhere along the route of lipid metabolism which result in elevated cholesterol levels. The present invention seeks to reduce cholesterol levels by administering therapeutic agents as described herein. Generally, the relevant disease states are those where iii vivo cholesterol levels are above the desired cut off for the particular clinical situation of the patient. Obviously, the level can vary depending upon the age, gender, genetic background and health of the patient.

Examples of disease suitable for treatment according to the present invention are familial lipoprotein lipase deficiency, an autosomal recessive disorder, familial apolipoprotein C-II deficiency, an autosomal recessive disorder; familial hypertriglyceridemia, an autosomal dominant disorder; familial defective apolipoprotein B-100; and familial combined hyperlipidemia. All of these lipid-related diseases can lead to elevated cholesterol levels. However, the most common cause of high blood cholesterol is due to familial hypercholesterolemia (FH). FH is an autosomal dominant disorder caused by a mutation in the gene encoding the LDL receptor protein. Five classes of mutant alleles have been identified that cause a functional or absolute LDL receptor deficiency. Treatment of all of these diseases is contemplated as part of the present invention. Thus, a step of identifying individuals with these diseases may be included as part of any therapeutic method disclosed herein.

The drugs administered to achieve these therapeutic goals are selected RXR and LXRα agonists that are capable of reducing lipid adsorption and increasing bile acid synthesis, respectively, in vivo. Many of these compounds are known for other indications, and may be applied here upon screening for the appropriate activity, as set forth above. For example, the rexinoid LG268 is suitable for treatments aimed at reducing cholesterol adsorption. Additionally compounds that may prove useful may be found in U.S. Pat. No. 5,455,265 and U.S. Pat. No. 5, 780,676, each specifically incorporated herein by reference in its entirety.

Therapies also may encompass diagnostic procedures to establish the need for a particular therapeutic regimen. Methods for determining cholesterol levels are well known, widely practiced, and many commercial kits are readily available. It also is envisioned that continued monitoring of cholesterol levels throughout a course of treatment will be utilized, both to assess the efficacy of the treatment, and to establish whether an increase or descrease in the drug dosage is required.

II. Combination Therapies

In certain embodiments, the combined administration of cholesterol adsorption inhibitors with other drugs can prove particularly advantageous. Other compounds that may be used in conjunction with RXR agonists that reduce cholesterol adsorption are (a) LXRα agonists, or (b) one or more of the three classes of antilipemic agents currently in use for treating lipid disorders, or both (a) and (b). The three groups of antilipemic drugs are classified as (i) bile acid sequestrants, (ii) fibric acid derivatives and (iii) HMG-CoA reductase inhibitors.

Examples of bile acid sequestrants are Colestid™, LoCholest™, and Questran™. Colestid™ is colestipol hydrochloride, and is used primarily to reduce LDL-cholesterol. A single dosage is 5 grams of the powedered product, with one or two doses per day at the beginning of treatment, moving to one dose a day. Regimens are one to two months in duration. If necessary, dosage may be increased up to six doses per day in the absence of toxicity. The active ingredient of LoCholest™ and Questran™ is cholestyramine resin, and is used as an adjunctive therapy for elevated serum cholesterol. One dose is 9 grams of the powdered product, administered once or twice per day and increaing to 4 doses daily. Increases are recommended at intervals not less than four weeks.

Fibric acid derivatives are Atromid-S™ and Lopid™. Atromid-S™ contains ethyl 2-(p-chlorophenoxy)-2-methyl-propionate and lowers triglyceride levels. Daily dosage for adults is 2 grams, divided into two doses. The active ingredient Lopid™ is gemfibrozil. It acts by reducing serum triglycerides and LDL-cholesterol. Dosage is 600 mg, twice daily, before the morning and evening meals.

HMG-CoA reductase inhibitors are Pravachol™ (pravastatin), Baycol™ (cervistatin), Lescol™ (fluvastatin), Lipitor™ (atorvastatin) (lovastatin) Mevacor™ (lovastatin), Zocor™ (simvastatin) and other of the so-called "statins." Dosages for each of these compounds are well known to the skilled artisan and can be found, for example, in the Physician's Desk Reference, 52nd Ed., MEDICIAL ECONOMICS Co. (1 998).

These compounds may be given together, or sequentially as part of a treatment regimen. For example, a combination therapy may involve alternating administrations of two agents (A, B, A, B, A, B . . . ) or three agents (A, B. C, A, B, C . . . ). Both of these embodiments are considered variations of combination therapies. Typical intervals between different therapies range from one hour to a week or even a month. However, intervals of about 24 to 48 hours are envisioned as particuarly useful.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods for Preparation and Study of LXRα Knockout Mice

Construction of the LXRα Targeting Vector

Mouse LXRα genomic clones were obtained by screening a 129Sv λ genomic library using the 1.4 kb full-length cDNA of human LXRα (Willy et al., 1995). The targeting vector was constructed using a neo-TK template plasmid containing a neomycin and two tandem herpes simplex virus thymidine kinase cassettes (Rosahl et al., 1993). This vector was designed to replace exons 3–6 by homologous recombination, which contain the complete DNA-binding domain and majority of the ligand-binding domain of LXRα (amino acids 86–327). A short arm was generated by blunt end inserting the 1.9 kb EcoRI-ApaI fragment containing exons 1 and 2 into the unique BamHI site 5' of the neo cassette, and the longer arm by blunt end inserting the 4.0 kb NcoI fragment containing exons 7–9 into the unique XhoI site located between the neo and TK cassettes. The targeting vector was linearized at a unique SalI site prior to electroporation.

Generation of LXRα Null Mice

Ablation of the mouse Lxrα gene locus was accomplished according to previously described methods (Ishibashi et al., 1993; Rosahl et al., 1993). SM-1 mouse ES cells were grown on irradiated STO feeder cells. Approximately $5 \times 10^7$ cells were electroporated with 1 mg/ml of linearized targeting vector and subjected to selection with G418 and FIAU. Resistant clones were analyzed by Southern blotting after HindI digestion. Two positive clones were expanded and injected into C57BL/6 blastocysts to produce five male chimeric mice, which transmitted the mutant gene through the germline. The mice were genotyped by Southern blotting of tail DNA after EcoRI digestion. Subsequent experimental procedures were performed on the C57BL/6-129Sv mixed strain descendants (F2 and subsequent generations) and repeated with the second clone, with the exception of the 90-day 2% cholesterol diet. The mice were maintained on a 12 hr lighted hr dark cycle and fed ad libitum a standard, cereal-based mouse/rat diet (No, 7001, Harlan Teklad) containing 4% (w/w) fat and approximately 0.02% (w/w) cholesterol. Where indicated, this diet was supplemented with 0.2% or 2% (w/w) cholesterol (ICN). The mice were euthanized after a 5 hr fast during the early phase of the light cycle unless otherwise indicated. All mouse procedures used in this study were performed in accordance with the Institutional Animal Care and Research Advisory Committee at the University of Texas Southwestern Medical Center at Dallas.

Northern Blotting

Total RNA wee extracted using RNA STAT-60 (Tel-Test, Inc.), and mRNA isolated using oligo(dT)-cellulose columns (Pharmacia Biotech). Equivalent amounts of mRNA from 4–6 mice were pooled, and 4–10 μg subjected to Northern blot analysis as described (Lehrman et al., 1987). Mouse cDNA probes for Lxrα and Lxrβ (Lehrman et al., 1997; cholesterol 7α-hydroxylase (Ishibashi et al., 1996); oxysterol 7α-hydroxylase (Schwarz et al., 1997); PPARα, PPARβ, PPARγ(Kliewer et al., 1994); and 15 other lipid regulatory genes (Shimano et al., 1997) were prepared as described. Sr-B1 cDNA probe was a gift from Dr. Helen Hobbs. Probes for SCAP and sterol carrier protein were prepared by RT-PCR with mouse liver poly(A)$^+$ RNA as described previously for other probes (Shimano et al., 1996). PCR™ primers used were: SCAP, 5'-TTAAGCTTTGT CCCGGGCATTCCAACTGG-3' (SEQ ID NO: 1) and 5'-TTGAATTCGACTTGGTGAGCACCAACACAT-3' (SEQ ID NO:2); and sterol carrier protein, 5'-AAGAA GCTTGAAGAGGAAGGGGAA-3' (SEQ ID NO:3) and 5'-AGCTTAGCTTTGTCCGGCTGAAG -3' (SEQ ID NO:4) (Mori et al., 1991). Northern were quantitated using a phosphorimager (Molecular Dynamics) and standardized against β-actin controls.

Histological Procedures

Liver, kidney, spleen, adrenal, small intestine, brain, testis, ovary, skin, muscle, white and brown adipose tissue, heart, and lung tissue were fixed in formalin (Accustain; Sigma), embedded in paraffin wax, sectioned, and stained with hematoxylin and eosin by a standard procedure. Frozen tissue sections were stained with oil red O using standard procedures. Sections were examined under bright-field microscopy with an Olympus model BX50 photomicroscope.

Plasma and Tissue Chemical Analyses

Mice were anaesthetized with sodium pentobarbital and exsanguinated via the ascending vena cava. Blood was transferred to tubes containing EDTA (Microcuvette CB 1000 capillary tubes; Sarstedt, Inc.), and the plasma isolated by centrifugation. Pooled plasma (from five mice) was analyzed for cholesterol, triglyceride, and lipoproteins as previously described (Ishibashi et al., 1993). Whole livers were removed, weighed, and sections taken (0.2 9) for lipid analysis. The lipids were extracted and analyzed for triglycerides and cholesterol as previously described (Bucolo and David, 1973; Yokode et al., 1990). Plasma analysis of glucose, aspartate aminotransferase, alanine aminotransferase, cholesterol, triglycerides, albumin, and total protein levels was performed using a Paramax RX automated analyzer (Dade International).

Bile Acid Analyses

In studies involving the measurement of bile acid pool size, composition, and excretion, male mice were housed individually in plastic cages containing wood shavings and were fed their respective diets ad libitum. Stools were collected from each animal over the 72 hr immediately prior to study, dried, weighed, and ground in a mechanical blender. Aliquots were taken for the measurement of total bile acid content by an enzymatic method as described (Turley et al., 1997). The daily stool output (g/day per 100 g body weight) and fecal bile acid content (μmol/g) were used to calculate the rate of bile acid excretion (Monday per 100 9 body weight). After the mice were weighed, anesthetized, and exsanguinated, the entire small intestine and its contents, along with the bulk of the liver and the gallbladder, were combined and extracted in ethanol with [24-$^{14}$C] taurocholic acid (New England Nuclear) added to correct for procedural losses. The total bile acid content of the extract was quantitated by HPLC. These data, together with the respective value for recovery of the internal standard, were used to calculate bile acid pool size (μmol/100 g body weight) and composition. Irrespective of genotype or diet, taurocholic acid and tauromuricholic acid accounted for more than 95% of the bile acids in the pool in all cases. No attempt was made to resolve what fraction of the muricholic acid peak corresponded to β, α, and $\bar{\omega}$ forms of this bile acid.

Cell Culture and Cotransfecton Assays

Transient transfections in Hepa1-6 mouse liver cells were performed as described (Willy et al., 1995). Cells were maintained at 5% $CO_2$ in DMEM supplemented with 10% fetal bovine serum. Receptor expression plasmids encoding mouse LXRα or LXRβ in CMX vectors were cotransfected with a luciferase reporter plasmid (TK-CYP7A-LXREx3-LUC) containing three tandem copies of the DR-4 sequence (gcttTGGTCActcaAGTTCAagtta, SEQ ID NO:5) from the rat Cyp7a gene (Chiang and Stroup, 1994). 24(S),25-epoxycholesterol was dissolved in ethanol and added to cells after transfection in medium containing 5% cabosil-treated newborn calf serum. All transfections were normalized to a β-galactosidase internal standard as a control. Data are presented as mean relative light units (RLUs) from triplicate assays±SEM.

Statistical Analyses

Values are expressed as mean ± standard error of the mean (SEM). The significance of differences between mean values were evaluated using the unpaired Student's t-test. Sample groups showing heterogeneity of variance were appropriately transformed before analysis Example 2

Targeted Disruption of the Lxrα Gene

The mouse Lxrα gene includes nine exons that encompass the translated portion of the gene. Exons 1 and 2 encode the amino-terminal portion of the receptor (A/B encode the hinge and ligand-binding domains (D and E regions). A targeting construct was prepared by inserting a PGK-neo cassette between an ApaI site at the beginning of exon 3 and an NcoI site in the intron between exons 6 and 7. Homologous recombination of this construct in SM-1 ES cells replaced exons 3–6 encoding the DNA-binding and ligand-binding domains of LXRα (amino acids 86–327). Two ES cell clones were chosen for generation of chimeric, heterozygous (LXRα (+/−)) and homozygous (LXRα (−/−)) mice. Mutant mice were viable and fertile, and they externally appeared normal when reared under normal laboratory conditions on standard rodent chow. Under these conditions, heterozygous and homozygous animals lived normal lifespans and bred with predicted Mendelian distributions. Analysis of liver mRNA from these mice revealed that heterozygotes retain significant levels of LXRα transcripts (50% of wild type), while no wild-type transcripts are detected in homozygous mice. In addition, no LXRα protein was detected in homozygotes by immunoblot analysis using antibodies specific for the hinge region of LXRα. The inventors conclude that this disruption results in mice that are null for LXRα.

Example 3

Hepatomegaly and Cholesterol Accumulation in LXRα Null Mice

Previously, the inventors and others have shown that LXRs are activated by a specific group of monooxidized metabolites of cholesterol, including 22(R)-hydroxycholesteroll 24(S)-hydroxycholesterol, and 24,25 (S)-epoxycholesterol (Janowski et al., 1996; Lehrman et al., 1997). The fact that these metabolites are naturally occurring and are elevated in tissues where cholesterol metabolism is high (e.g., the liver) led to the prediction that LXRs may have a role in the regulation of cholesterol metabolism. Since wild-type murine species have an extraordinary capacity to ingest large quantities of cholesterol without deleterious effects (Breslow, 1996), one hypothesis the inventors wished to explore was whether LXRα null mice had a defect in their ability to respond to dietary cholesterol. To test that idea, 2–3 month old, gender-matched LXRα wild-type and null mice were characterized after being reared on diets containing different cholesterol concentrations for 0, 7, 30, and 90 days. Analysis of LXR— (−/−) animals fed a standard laboratory rodent chow indicated these mice appeared identical to their wild-type littermates as determined by morphological and histological studies (see below). In retrospect, the lack of a gross phenotype on this diet in the mutant mice is perhaps not surprising, since standard rodent chow contains relatively little cholesterol (≦0.02% w/w). On this diet, the cholesterol requirement of these animals is achieved primarily through de novo biosynthesis (Osono et al., 1995).

The inventors next treated the effect of a diet rich in cholesterol (chow supplemented with 2% cholesterol). On a per diem basis, the intake of cholesterol on this diet is approximately 20–30 times above the amount an average animal synthesizes to maintain homeostasis when its dietary needs are not being met (Osono e! al., 1995). In contrast to wild-type animals, which can sustain this cholesterol-rich diet indefinitely without deleterious effects, there were dramatic morphological, histological, and chemical changes in the livers of LXRα null mice fed the same diet. Within 7 days of beginning the 2% cholesterol diet and chronically worsening over a 90day period, there was a prominent color and size change in the LXRα (−/−) vs wild-type livers.

Histological examination of these livers demonstrated the presence of a time-dependent increase in the number and size of intracellular vacuoles, characteristic of lipid deposits. Oil red O staining of liver sections verified the deposition of increasing quantities of lipid by 7 and 30 days. After 90 days, the morphology of the LXRα (−/−) livers had been substantially altered, and there was distinct evidence of increased hematopoietic foci, macrophage infiltration, and progressive hepatocellular degeneration. Chemical analysis of these livers showed that, consistent with the distinct color change, all of the accumulated lipid is in the form of cholesterol, 75% of which is esterified. Remarkably, the LXRα null animals exhibited a 15- to 20-fold increase in hepatic cholesterol within just 7 days of feeding the cholesterol-rich diet. Both liver mass and cholesterol concentration continued to increase with time, and by 90 days the LXRα (−/−) livers had doubled in mass and were in the advanced stages of failure. Consistent with the known ability of wild-type animals to adapt quickly to cholesterol-rich diets, the livers of LXRα (+/+) animals maintained essentially normal appearance and function. In these animals, there were no significant changes in liver histology or size, and only nominal increases in hepatic cholesterol were detected. Interestingly, there was an increase in hepatic triglyceride levels in wild type, but not LXRα null mice. The elevated hepatic triglyceride level seen in the wild-type mice explains the slight pigment change in the livers of these animals, even though their cholesterol levels remained low.

To confirm the dietary dependence of the defect seen in LXRα (−/−) mice, a second group of wild-type and homozygous animals was analyzed after 7 and 22 days on an intermediate cholesterol diet (chow supplemented with 0.2% cholesterol). On this diet, the average animal consumes an amount of cholesterol per day that is approximately twice what it needs to maintain normal homeostasis. LXRα (−/−) mice accumulated hepatic cholesterol to levels 3- and 10-fold higher than wild-type mice when fed a 0.2% cholesterol diet for 7 and 22 days, respectively. A comparison of mice on the 0.2% cholesterol diet vs. mice on the 2% cholesterol shows that the defect in LXRα (−/−) mice causes a near linear accumulation of hepatic cholesterol, regardless of whether the diet contains 0.2% or 2% cholesterol. These results demonstrate that, in the absence of LXRα, mice are unable to tolerate any dietary cholesterol in excess of what they can synthesize de novo.

Similar dietary studies were performed using heterozygous mice, which express approximately half of the levels of LXRα. These mice displayed an intermediate phenotype, accumulating hepatic cholesterol concentrations to levels between those observed for LXRα (+/+) and (−/−) mice. These results indicate that expression levels of LXRα are crucial for a complete response.

Significantly, there were no changes in the body weights of either LXRα (−/−) or (+/+) mice, irrespective of the type or length of the diet. However, there was a noticeable decrease in the amount of white adipose tissue in LXRα (−/−) mice after 90 days on the 2% cholesterol diet, which likely compensated for the net increase in liver mass. Morphological and histological examinations of several other tissues where LXRα is expressed, including kidney, small intestine, spleen, and adrenal, are ongoing, but preliminary results have revealed no obvious abnormalities in these tissues thus. To date, no gender-specific phenotypic differences have been observed in LXRα knockout mice, although female mice tend to have higher basal and diet-induced cholesterol levels.

Analysis of the plasma from the animals used in the above dietary studies confirms and extends the conclusion that LXRα null animals have a crucial defect in hepatic metabolism of dietary cholesterol (Table 3). Plasma cholesterol levels rose significantly (>200%) over the course of the 90-day, high-cholesterol diet in LXRα (−/−) mice, while wild-type mice characteristically showed no change. There was also a dramatic increase in the levels of alanine and aspartate amino transferases (26- and 7-fold, respectively, within 30 days) in the serum of the LXRα (−/−), but not wild-type animals. These enzymes are predominantly expressed in the liver, and the large increase in their levels in serum is indicative of hepatocyte injury and necrosis and is consistent with the results of the histological studies. By 90 days, the LXRα (−/−) livers deteriorated to the point where they have lost much of their normal cell structure, and this change was reflected by the observed decrease (between 30 and 90 days) in the levels of amino transferases still present in the serum of these animals (Table 3). Commensurate with impaired liver function, LXRα null mice exhibited a time-dependent decrease in serum glucose to half the normal level of their wild-type littermates when fed the high-cholesterol diet. Although several other parameters in the plasma, including triglycerides, total protein, albumin, creatinine, and electrolytes appeared normal, these results demonstrate that significant liver damage has occurred by 90 days and suggest that extension of this diet will ultimately result in complete liver failure.

A characteristic of murine species is their ability to regulate intermediate and low-density lipoprotein (IDL/LDL) cholesterol in serum tightly even under prolonged conditions of elevated cholesterol intake. Since the data from Table 3 revealed an increase in plasma cholesterol in the LXRα null mice, a plasma lipoprotein profile was generated from wild-type and homozygous mice fed standard or 2% cholesterol chow diets for 30 days. As predicted, wild-type animals were resistant to large increases in dietary cholesterol and maintained very low circulating levels of IDL/LDL cholesterol. However, LXRα (−/−) animals produced an 5-fold increase in IDL/LDL cholesterol and only minimal changes in HDL when compared to LXRα (+/+) animals fed the 2% cholesterol-supplemented diet.

TABLE 3

Plasma Analysis of Wild Type and LXRα (−/−) after 2% Cholesterol Diets

| Test | Genotype | 0 Days | 7 Days | 30 days | 90 Days |
|---|---|---|---|---|---|
| Cholesterol | +/+ | 84 | 82 | 105 | 82 |
| (mg/dL, ±<3.5%) | −/− | 72 | 127 | 162 | 145 |
| Alanine transaminase | +/+ | 17 | 19 | 13 | 15 |
| (U/L, ±<5.5%) | −/− | 12 | 98 | 314 | 188 |
| Aspartate transaminase | +/+ | 39 | 44 | 41 | 45 |
| (U/L, ±7%) | −/− | 44 | 160 | 303 | 197 |
| Glucose | +/+ | 231 | 247 | 200 | 219 |
| (m/dL, ±<3%) | −/− | 178 | 195 | 109 | 121 |
| Triglycerides | +/+ | 52 | 38 | 39 | 43 |
| (mg/dL, ±<5%) | −/− | 46 | 35 | 29 | 31 |
| Total protein | +/+ | 4.7 | ND | 4.4 | 4.4 |
| (g/dL, ±<4%) | −/− | 4.6 | 4.7 | 5.4 | 4.7 |
| Albumin | +/+ | 1.7 | 1.5 | 1.5 | 1.5 |
| (g/dL, ±<3%) | −/− | 1.6 | 1.6 | 1.6 | 1.4 |

Example 4

Cholesterol and Bile Acid Metabolism Defects in LXRα Null Mice

The phenotype described above provides convincing evidence that one of the roles of LXRα is to regulate dietary cholesterol metabolism in the liver. Since the primary pathway for catabolic elimination of cholesterol is through bile acid metabolism, the inventors next examined the response of several important components in this pathway. An 8-day dietary study similar to the one described above was performed on 3-month-old male mice, comparing wild-type and LXRα (−/−) animals fed standard or 2% cholesterol-supplemented chow. The animals in this group were analyzed for rates of fecal bile acid excretion, and bile acid pool size and composition. Similar to the results obtained above, LXRα (−/−) animals manifest a 16-fold increase in hepatic cholesterol when fed a 2% cholesterol chow diet.

Within 8 days, the concentration of hepatic cholesterol rose in LXRα null mice from its normal value of 2.46±0.05 mg/g to 40.09±0.82 mg/g tissue, whereas hepatic cholesterol in wild-type mice increased nominally from 2.21±0.03 mg/g to 5.03±0.19 mg/g tissue. Interestingly, even on the low-cholesterol diet there was a statistically significant difference (P<0.001) between the hepatic cholesterol concentration in LXRα (+/+) and (−/−) mice (2.21±0.03 and 2.46±0.05 mg/g, respectively). These phenotypes were independent of gender.

The ability of wild-type animals to maintain a relatively low hepatic cholesterol concentration when cholesterol intake is high is largely due to the compensatory increase in bile acid synthesis. The 123% increase in fecal bile acid excretion and 36% increase in bile acid pool size were substantial and expected, based on previous studies showing that bile acid metabolism is responsible for metabolic clearance of dietary cholesterol (Carey and Duane, 1994; Schwarz et al. In marked contrast, the bile acid pool size of the LXRα (−/−) mice was significantly lower than wild-type mice and did not change when the animals were fed the cholesterol-rich diet. In addition, bile acid excretion in the LXRα (−/−) mice increased less than half the amount it did in wild-type animals. Since ordinarily bile acid excretion reflects bile acid synthesis, these results imply that LXRα null mice have a decreased ability to up-regulate bile acid synthesis.

An analysis of bile acid pool composition revealed a striking difference in this parameter as well. Over 95% of the murine biliary bile acid pool is composed of cholic and muricholic acids (Akiyoshi et al., 1986). The ratio of cholic acid to muricholic acid is tightly regulated and has a significant effect on the animal's ability to absorb cholesterol in the intestine; the higher the ratio, the more cholesterol that is potentially capable of being absorbed (Cohen et al., 1977; Uchida et al., 1980). As shown in, wild-type animals respond to increased dietary cholesterol by substantially lowering this ratio (from 1.34±0.08 to 0.88±0.05). In contrast, LXRα (−/−) mice have a significantly higher basal ratio (2.03±0.23), which is completely unresponsive to increased cholesterol (2.2135 0.57). The above results are consistent with the notion that LXRα (−/−) mice lack a cholesterol-sensing mechanism that governs the clearance of excess cholesterol through bile acid synthesis.

Example 5

Regulation of Cyp7a by LXRα

The rate-limiting step in the classical bile acid synthesis pathway utilizes the liver-specific enzyme cholesterol 7α-hydroxylase. (Cyp7a), which converts cholesterol into 7α-hydroxycholesterol (Russell and Setchell, 1992). In marine species, this enzyme is transcriptionally regulated by dietary cholesterol (Rudling, 1992), and the inventors and others have shown that the Cyp7a promoter contains a functional LXR response element (i.e., LXRE) (Lehmann et al., 1997; see also below). In addition to Cyp7a, a second enzyme called oxysterol 7α-hydroxylase (Cyp7b) exists as part of an alternative bile acid synthesis pathway, which is not transcriptionally regulated by cholesterol (Schwarz et al., 1997). Therefore, it was of interest to characterize the response of these genes in the LXRα (−/−) mice. As expected, Cyp7a mRNA was up-regulated (5.9-fold) in wild-type mice fed a high-cholesterol diet for 7 days. However, there was no cholesterol-induced up-regulation of Cyp7a in LXRα (−/−) mice, consistent with the notion that this gene is a direct target of LXRα action. In contrast to Cyp7a, there were no differences in expression of Cyp7b in either LXR (+/+) or (−/−) mice.

In addition to normally expressing LXRα, the liver also expresses the closely related receptor, LXRβ. Since both of these receptors have similar ligand specificities (Janowski et al., 1996; Lehmann et al., 1997), the inventors wished to address why LXRβ cannot rescue the bile acid phenotype in LXRα (−/−) mice. The expression of the Lxrα and β genes is not regulated by dietary cholesterol, indicating that the LXRs are not likely to be auto-regulated in the liver. More importantly, there was no compensatory increase in the level of hepatic LXRβ in LXRα (−/−) mice. Furthermore, cotransfection studies with LXRα and β expression plasmids demonstrate that the LXRE found in the Cyp7a promoter is a substantially stronger response element for LXRα than it is for LXRβ. These results corroborate the previous findings of Lehmann and coworkers, showing that LXRα has a substantially higher affinity than LXRβ for binding to the Cyp7a LXRE (Lehmann et al., 1997). Taken together with the striking phenotype of LXRα (−/−) mice, the inventors conclude that LXRα and β can differentially regulate gene expression and, thus, may have non-overlapping roles.

Example 6

Impaired Expression of Hepatic Genes Involved in Multiple Lipid Pathways

In addition to the genes involved in bile acid metabolism, the expression of 18 other genes involved in cholesterol and fatty acid metabolism were investigated by Northern blot analysis. End product repression of cholesterol biosynthesis is a well-studied pathway that is controlled primarily by the transcription factor SREBP-2 (Brown and Goldstein, 1997).

As expected, the liver mRNA levels of SREBP-2, as well as the cholesterogenic enzymes, hydroxymethyl glutaryl-coenzymeA (HMG-CoA) synthase and reductase, farnesyl diphosphate (FPP) synthase, and squalene synthase were down-regulated in response to cholesterol in both LXRα (+/+) and (−/−) animals. Surprisingly, however, there was a significant increase in the expression of these genes in the LXRα (−/−), but not wild-type, animals fed a low cholesterol diet. At present, the consequence of the altered up-regulation of these genes is not fully understood and will require further study; however, the lack of a severe phenotype under low dietary cholesterol conditions suggests this misregulation may not be deleterious. Furthermore, no differences were seen in the regulation of SREBP cleavage activating protein (SCAP), sterol carrier protein, LDL receptor, HDL receptor (SR-B1), or apolipoprotein gene expression in the LXRα null mice.

In contrast to the up-regulation of genes involved in cholesterol biosynthesis, three genes involved in fatty acid metabolism, SREBP-1, stearoyl CoA desaturase-1, and fatty acid synthase, were markedly down-regulated in LXRα (−/−) mice on the low-cholesterol diet. Again, the consequence of the altered expression of these genes on this diet does not appear to be deleterious, but further study will be required to determine if there are other metabolic defects in these mice under other dietary conditions (e.g., low or high fatty acid supplemented diets). The expression of several other genes, including the three peroxisome proliferator activated receptors (PPARs) and acetyl CoA carboxylase were unchanged in the mutant vs wild-type mice.

Example 7

LG268 Prevents Liver Accumulation of Cholesterol in Both LXRα Wild-type and Knockout Mice Strains.

Male, A129 strain mice (LXRα +/+ and −/−) were fed Teklad 7001 powdered diet supplemented with 0.2% cholesterol 0.015% LG268 (provides 30 mg/kg body weight), vehicle, or 2% surfomer (a surfactant polymer that inhibits cholesterol absorption, Turley et al., 1991) ad libitum for 10 days. Animals were sacrificed and a liver aliquot was saponified and extracted and the cholesterol content was determined by gas chromatography using stigmastanol as an internal standard (Turley et al., 1994). Liver cholesterol accumulation was prevented by ingestion of LG268 in both LXRα knockout and wild-type mice. The two most likely mechanisms for this effect are (1) increased cholesterol output by enhanced bile acid production and secretion and/or (2) decreased cholesterol input by diminished cholesterol absorption.

Example 8

LG268 does not Prevent Liver Accumulation of Cholesterol by Increasing Bile Acid Production and Excretion.

Female, mixed strain (LXRα +/+ and −/−) mice were fed Teklad 7001 2% cholesterol (w/w) diet ad libitum for 7 days. Each day mice received a single bolus dose of LG268 (200 1/25 g mouse to provide 30 mg/kg body weight) or vehicle by oral gavage. Mice were killed and liver cholesterol was determined as described in FIG. 1. Small intestine (with luminal contents) and gall bladder were extracted together to determine bile acid pool size and composition as described by Schwartz et al., 1998. Stools were collected over 3 days from the individually housed mice, dried, weighed and ground. Fecal bile acid content was determined by an enzymatic method (Turley et al., 1996). LG268 did not prevent the liver accumulation by increasing bile acid production (as reflected in bile acid pool size and excretion).

Example 9

LG268 Inhibits Cholesterol Absorption in LXRα Wild-type and Knockout Mouse Strains.

Male, A 129 strain mice (LXRα +/+ and −/−) were fed Teklad 7001 powdered diet supplemented with 0.2% cholesterol .015% LG268 (provides 30 mg/kg body weight), vehicle, or 2% surfomer ad libitum for 10 days. On day 7, mice received a gavage dose of [22,23-3H]b-sitostanol (American Radiolabeled Chemicals, St. Louis, Mo.) and [4-14C]cholesterol (Amersham) for the measurement of cholesterol absorption by the fecal isotope ratio method (Turley et al., 1994). Cholesterol absorption was completely inhibited in mice receiving a dose of 30 mg/kg body weight over 10 days, regardless of LXRα genotype. LG268 was more effective than surfomer, at a dose 130-fold lower than the surfomer administration. In light of the extreme potency of LG268, a dose-response analysis was performed.

Example 10

LG268 Inhibits Cholesterol Absorption in Wild-type Mice at Levels as Low as 1.4 mg/kg Body Weight (Equivalent to 0.0007% of the Diet (w/w)).

Male, A129 strain mice were fed Teklad 7001 powdered diet supplemented with 0.2% cholesterol and various levels of LG268 (providing 1.4 to 30 mg/kg body weight) or vehicle ad libitum for 10 days. On day 7, mice received a gavage dose of [22,23-3H]b-sitostanol (American Radiolabeled Chemicals, St. Louis, Mo.) and [4-14C]cholesterol (Amersham) for the measurement of cholesterol absorption by the fecal isotope ratio method (Turley et al., 1994). Liver cholesterol concentration was determined as by gas chromatography. LG268 is effective at doses as low as 1.4 mg/kg body weight (0.0007% of the diet) in preventing liver accumulation of cholesterol by inhibiting cholesterol absorption.

Example 11

LG268 Inhibits Cholesterol Absorption in Wild-type Mice While Exerting Little or No Effect on Total Lipid Absorption.

Figure 4:
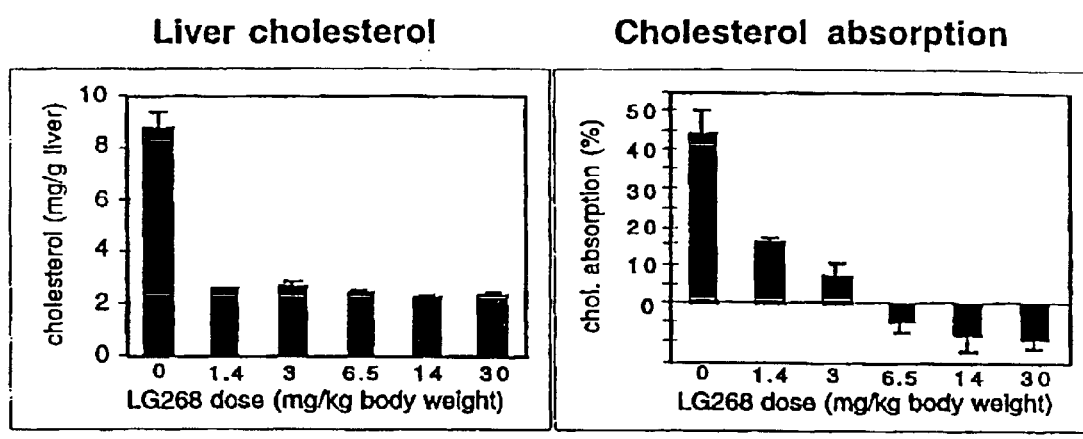
FIG. 4—Dose Response Curve for LG268 Inhibition of Cholesterol Absorption in LXRα Wild-Type Mice. Values represent mean ±SEM for 6 mice per group. LG268 given at 30 was given at the indicated dose for 10 days.
Figure 5:
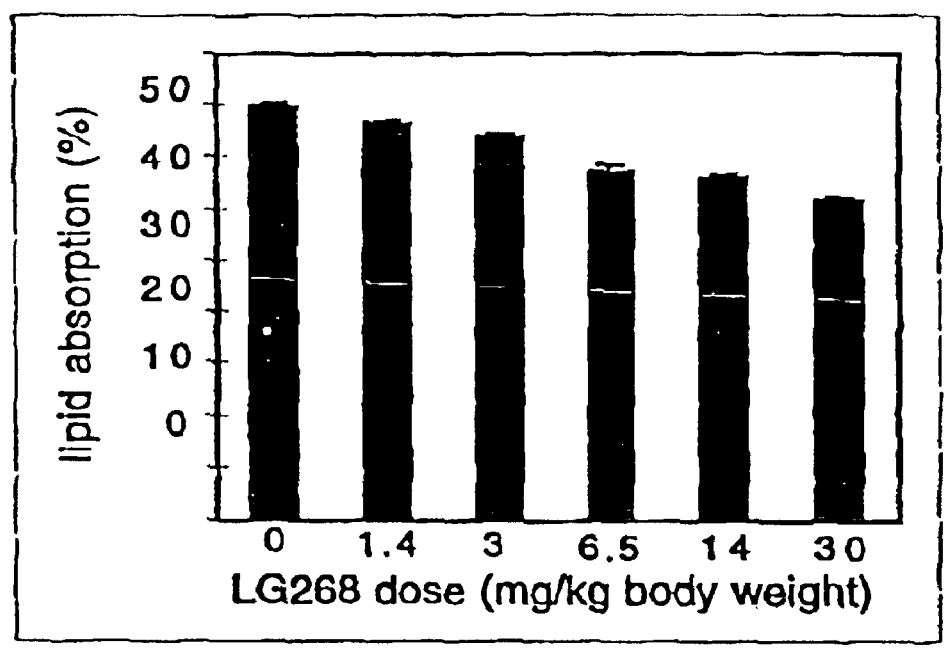
FIG. 5—Lipid Absorption in LXRα Wild-Type Mice Treated with LG268. Values represent mean ±for 5 mice per group. LG268 given at 30 mg/kg body weight for 10 days.
Figure 6:
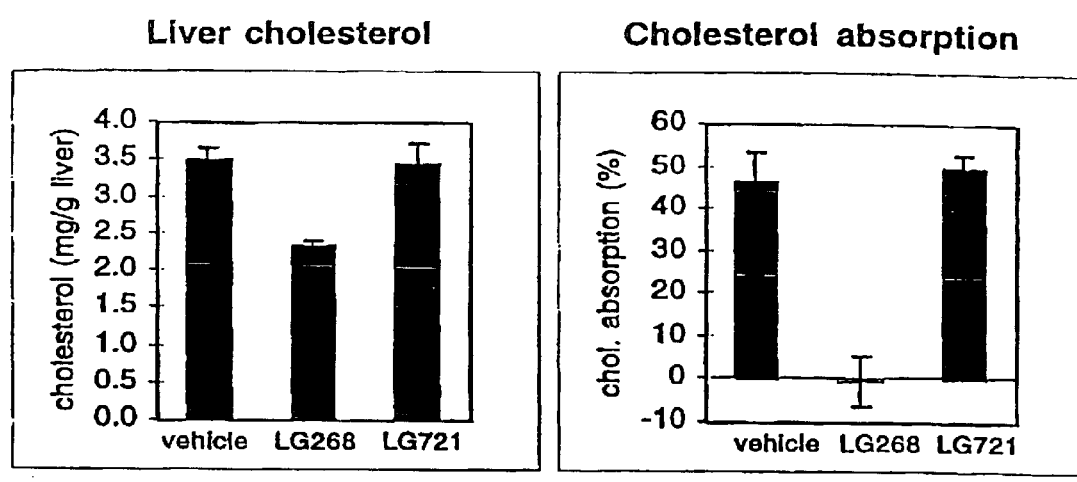
FIG. 6—Comparison of Different Rexinoids for the Ability to Reduce Liver Cholesterol and Cholesterol Absorption. Values represent the mean ±SEM for 5 mice per group. LG268 and LG721 given at 3 mg/kg body weight for 10 days.
Figure 7:
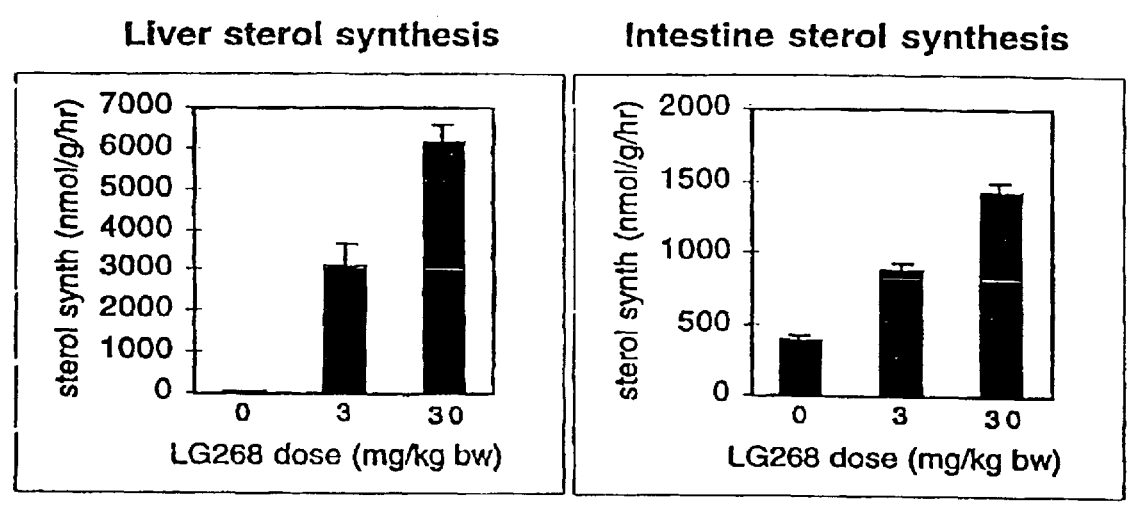
FIG. 7—Cholesterol Production in LXRα Wild-Type Mice Treated with LG268. Values represent mean ±SEM for 5 mice per group. LG268 given at 3 or 30 mg/kg body weight for 7 days.
Figure 8:
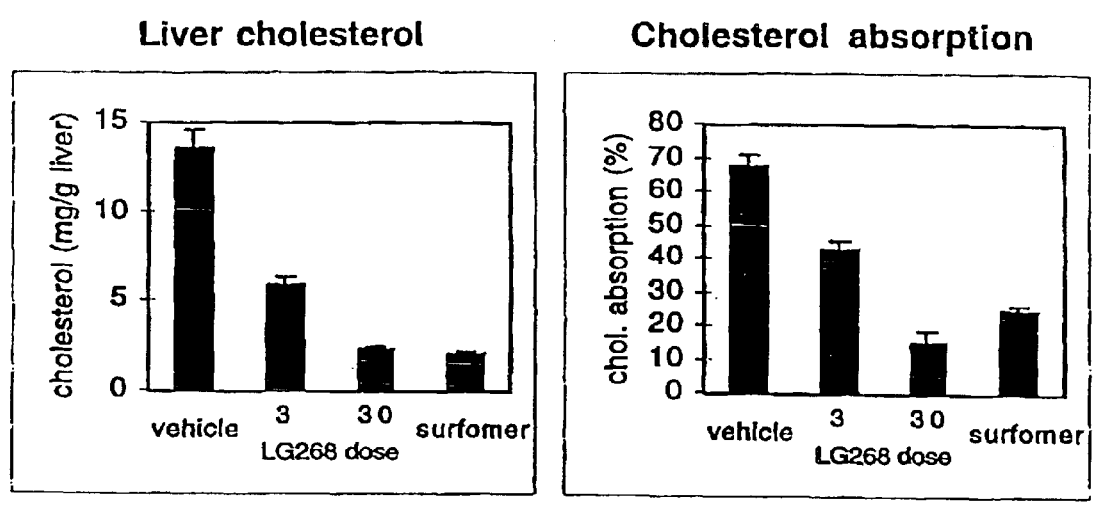
FIG. 8—Prevention of Liver Cholesterol Accumulation and Cholesterol Absorption by LG268 in Golden Syrian Hamsters. Values represent mean ±SEM for 6 hamsters per group, except for surfomer treatment, which contained 5 hamsters.
Figure 9:
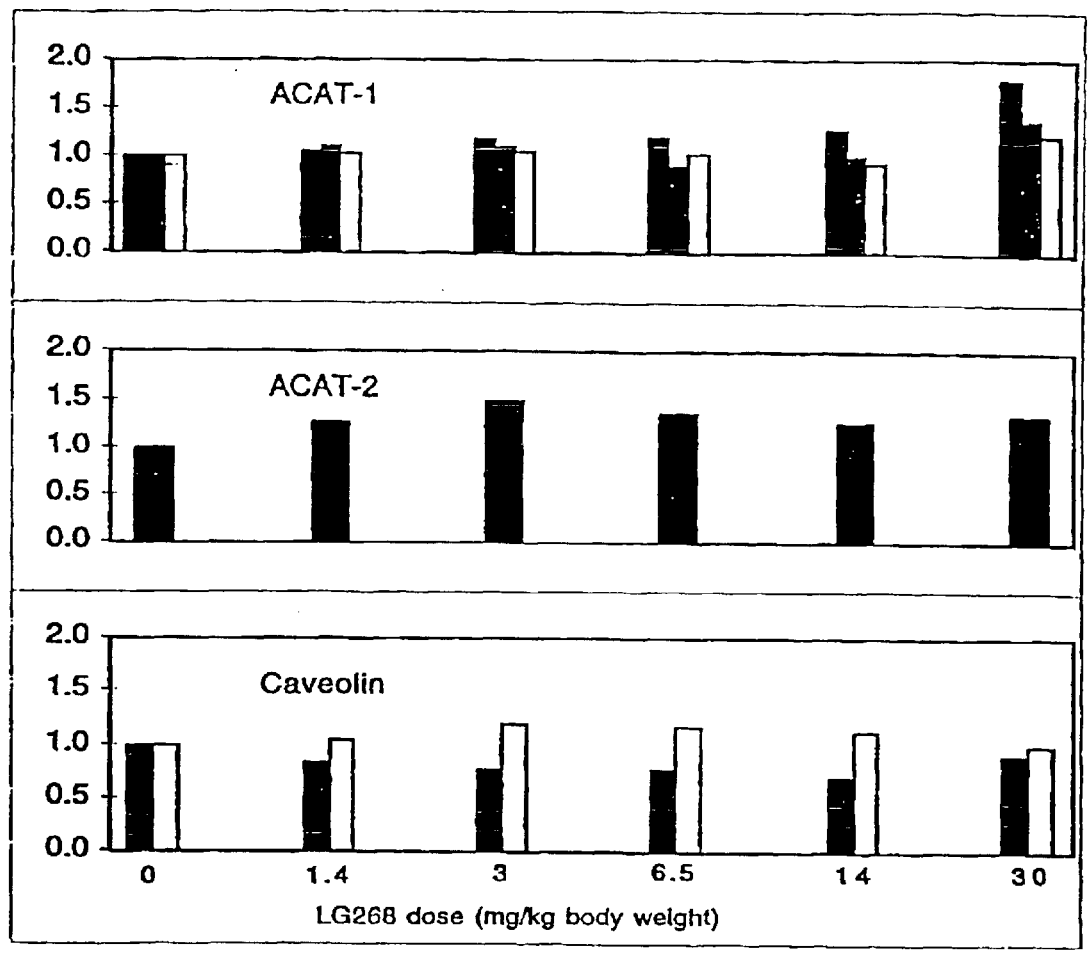
FIG. 9—Expression of Cholesterol-Related Genes in Duodenal Intestine Samples Treated with LG268. Values represent mean ±SEM for 5 mice per group. LG268 was given at the indicated dose for 10 days. Northern analysis was performed on duodenal intestinal samples.

Total lipid absorption was determined in the study described above (FIG. 4) to establish whether LG268 effects were specific to cholesterol or were affecting lipid absorption or intestinal integrity. Total lipid absorption was determined gravimetrically (Schwartz et al., 1998) by establishing lipid intake (amount of food consumed over 72 hours× dietary lipid content) and lipid output (fecal lipid content× quantity of stool collected over the same 72 hours) to calculate the fraction of lipid consumed that was absorbed. Initial observations suggested that mice receiving LG268 were not experiencing general lipid malabsorption or steattorhea. Stool output was normal, and the feces did not appear greasy or malodorous. The gravimetric determination of lipid absorption shown in FIG. 5 confirmed these findings. The reduction in lipid absorption seen in these animals can be accounted for by the reduction in cholesterol uptake (cholesterol comprises ~5% of the lipid in these diets and is extracted and measured as lipid in these analyses). Therefore, the effects of LG268 are specific for cholesterol absorption.

Example 12

LG268 is Exerting Its Effects on Cholesterol Absorption Through an RXR-mediated Pathway.

Several agents that inhibit cholesterol absorption have been found to affect the physicochemical nature of the intesinal lumen, for example saponins precipitate cholesterol thereby making it unavailable for absoprtion. It would be unlikely that at the extremely low doses at which LG268 exerts its effects it could be causing such physicochemical changes. However, to rule out this possibility, a cholesterol absorption study was performed using LG268 (which binds and activates RXR) and LG721 (a structurally related compound that binds but fails to activate RXR). If LG268 was causing cholesterol precipitation or micellar disruption in the intestinal lumen, the structural analog LG721 would be predicted to do the same.

Male, A129 strain mice were fed Teklad 7001 powdered diet supplemented with days. On day 7, mice received a gavage dose of [22,23-3H]b-sitostanol (American Radiolabeled Chemicals, St. Louis, Mo.) and [4-14C]cholesterol (Amersham) for the measurement of cholesterol absorption by the fecal isotope ratio method (Turley et al., 1994). Liver cholesterol concentration was determined as by gas chromatography. LG721 fails to prevent liver cholesterol accumulation or inhibit cholesterol absorption. This would suggest that the activity of LG268 relies not on the small lipophilic nature of the molecule (shared by LG721), but by its unique capacity to bind and activate the retinoid X receptor.

Example 13

LG268 Inhibits Cholesterol Absorption so Effectively that Mice Compensate for the Lack of Exogenous Cholesterol by Raising Production of Endogenous Cholesterol in Liver and Other Organs.

Male, A129 mice were fed Teklad 7001 diet supplemented with 0.2% cholesterol and vehicle or LG268 (at 3 or 30 mg/kg body weight) for 7 days ad libitum. Rates of sterol synthesis were measured in vivo as described (Jeske and Dietschy, 1980, Turley et al., 1981) based on the incorporation of [$^3$H]water into digitonin-precipitable sterols over one hour. Mice treated for 7 days with LG268 exhibit increased cholesterol biosynthesis to compensate for the absense of an exogenous supply due to a block in cholesterol absorption. Increased synthesis was also observed in spleen, kidney, and carcass and in all tissues was LG268 dose-dependent and inversely correlated to cholesterol absorption capacity.

Example 14

LG268 Prevents Liver Cholesterol Accumulation and Inhibits Cholesterol Absorption in the Golden Syrian Hamster.

Hamsters provide a better animal model for cholesterol metabolism than mice (however, mice offer the advantage that they can be genetically manipulated, for example the LXRα −/− strain). Like humans, hamsters carry the bulk of their blood-borne cholesterol in LDL particles, and do not greatly respond to increased dietary cholesterol by increasing bile acid production and excretion. Male Syrian Golden hamsters were fed Teklad 7001 diet supplemented with 0.2% cholesterol and vehicle, LG268 (providing 3 or 30 mg/kg body weight) or 2% surforner. On day 7, they received a gavage dose of [22,23-3H]b-sitostanol (American Radiolabeled Chemicals, St. Louis, Mo.) and [4-14C]cholesterol (Amersham) for the measurement of cholesterol absorption by the fecal isotope ratio method (Turley et al., 1994). Stools were collected from the individually housed hamsters over the next 72 hours. On day 12 the animals were sacrificed and liver was removed for cholesterol determination by gas chromatography (Turley et al., 1994). LG268 was effective in hamsters in reducing liver cholesterol and inhibiting cholesterol absorption. Therefore the effects of LG268 on cholesterol homeostasis are not limited to mice, but observed in other mammalian species as well.

Example 15

LG268 does not Regulate the Expression of Several Genes Proposed to Affect Cholesterol Uptake and Processing by the Intestine.

It is known that exogenous cholesterol is taken up in the distal duodenum (and perhaps proximal jejunum) by the intestinal enterocyte, is rapidly esterified (by ACAT) and packaged into chylomicrons for transport into the lymphatic system (reviewed by Homan and Krause, 1997). Recently, caveolin has also been proposed to play a role in cholesterol trafficking in the intestine (Field et al., 1998). Disruption of any of these processes could result in diminished cholesterol absorption capacity. As LG268 is an agonist of the nuclear hormone receptor RXR, it is likely that the primary targets of this drug would be transcriptionally regulated and show a change in the steady state level of mRNA for critical target genes. Northern analyses were performed on duodenal intestine samples obtained in the experiment described in FIG. 4. Results were quantitated using a phosphoimager (Molecular Dynamics), standardized against b-actin controls, and mathematically adjusted to yield 1 unit for the vehicle-treated control group. No apparent change in ACAT-1, ACAT-2 or caveolin mRNA levels was observed in LG268-treated mice. This suggests that LG268 acts upon other novel gene targets involved in intestinal cholesterol metabolism. Since the mechanism of cholesterol absorption is unknown and is one of the key pathways regulating cholesterol homeostasis, these findings suggest rexinoids will be powerful tools to dissect the regulatory events that govern this important metabolic pathway.

Example 16

LG268 Regulates the Expression of the ATP-binding Cassette Protein-1 (ABC-1).

Figure 10A:
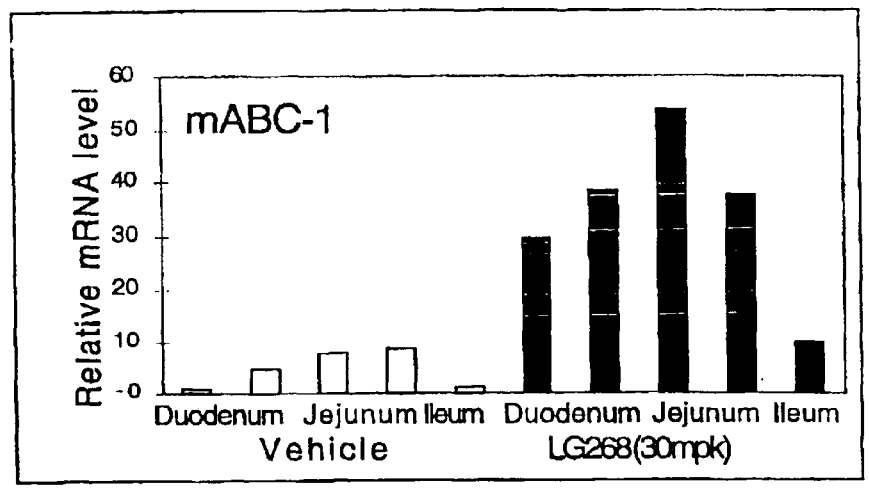
FIG. 10A and FIG. 10B.—Expression of ATP-Binding Cassette Protein-1 in Duodenal Intestine Samples Treated with LG268. Northern analysis was performed on intestinal samples following a 6 or 12 hour treatment with LG268 (30 mg/kg body weight). Northern gels were quantified using a phosphorimager, standardized against controls, and mathmatically to yield 1 unit for the vehicle-treated control group.
Figure 10B:
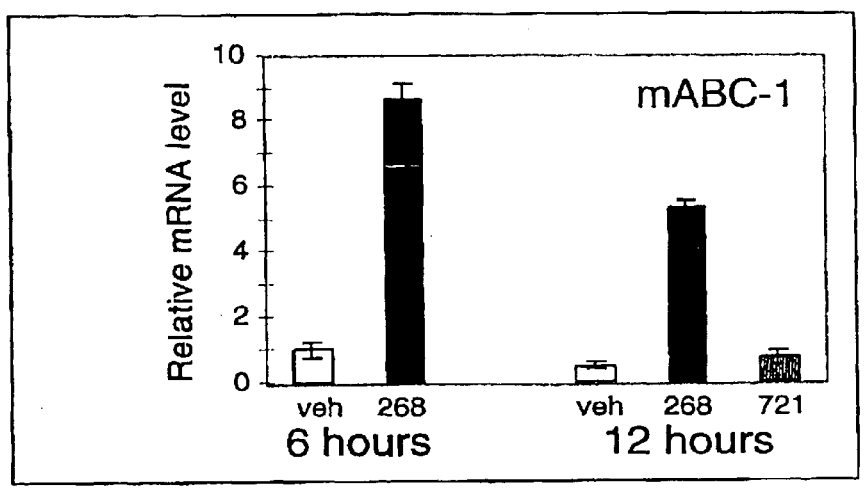

The ATP-binding cassette protein-1 is a newly described membrane protein implicated in reverse cholesterol transport, in other words the efflux of cholesterol from peripheral tissues to the liver (Young and Fielding, 1999; Tall, 1998). Defects in the ABC1 gene are responsible for Tangiers disease, a rare genetic disorder in which patients exhibit cholesterol-laden macrophages, premature atherosclerosis, and the complete absence of circulating HDL (Brooks-Wilson et al., 1999; Bodzioch et at., 1999; Rust et al., 1999). While it has been firmly established that ABC-1 is expressed in macrophage cells, the inventors now demonstrate that ABC-1 is produced in the mouse small intestine in a cephalocaudal distribution that corresponds to regions known to be involved in cholesterol absorption (FIG. 10A). Most importantly, ABC-1 expression is greatly increased in mice orally dosed with LG268 (30 mg/kg body weight) for as little as 6 hours (FIG. 10A and FIG. 10B).

Male A129 strain mice were fed Teklad 7001 powdered diet supplemented with 0.2% cholesterol and 0.015% LG268, equimolar LG721 (see example 12) or vehicle at 7 pm (beginning of dark cycle). Animals were sacrificed at 1 am (6 hour time point) or 7 am (12 hr), the intestine was removed and rinsed with ice-cold phosphate buffered saline, then subdivided into 5 segments of equal length (~8 cm each, FIG. 10A) or 3 segments (the proximal segment representing the duodenumis depicted in FIG. 10B). Intestinal mucosa was obtained from each segment and poly (A+) RNA isolated for northern analyses. Results were quantified using a phosphorimager, standardized against mactin controls, and mathematically adjusted to yield 1 unit for the vehicle-treated control group.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may he substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,697,899
U.S. Pat. No. 4,430,434
U.S. Pat. No. 4,559,302
U.S. Pat. No. 4,727,028
U.S. Pat. No. 4,960,704
U.S. Pat. No. 5,354,855
U.S. Pat. No. 5,455,265
U.S. Pat. No. 5,602,306
U.S. Pat. No. 5,639,940
U.S. Pat. No. 5,656,016
U.S. Pat. No. 5,720,936
U.S. Pat. No. 5,770,219
U.S. Pat. No. 5,779,708
U.S. Pat. No. 5,780,676
U.S. Pat. No. 5,783,208
U.S. Pat. No. 5,789,655
U.S. Pat. No. 5,797,898
EPO 0273085
Accad, M. and R. V. Farese, Jr. 1998. Cholesterol homeostasis: a role for oxysterols. Curr. Biol. 8: R601–R604.
Aklyoshi, Uchida, Takase, Nomura, Takeuchi, "Cholesterol gallstones in allaxan-diabetic mice," *J. Lipid Res.*, 27:915–924, 1986.
Alt, Kellems, Bertino and Schimke, *J. Biol. Chem.*, 253:1357. 1978.
Androlewicz et al., *Proc. Natl. Acad. Sci.* USA 91:12716–1 2720, 1994.
Arts et al., *Arterioscler. Thromb. Vasc. Biol.*, 17:26–32, 1997.

Baichwal et al., "Vectors for gene transfer derived from animal DNA viruses: Transient and stable expression of transferred genes," In: Gene transfer, Kucherlapati R, ed., New York: Plenum Press, pp. 117–148, 1986.

Bodzioch et al. "The gene encoding ATP-binding cassette transporter 1 is mutated in Tangier disease," Nat. Genet. 22:347–351, 1999.

Boehm, M. F., L. Zhang, L. Zhi, M. R. McClurg, E. Berger, M. Wagoner, D. E. Mais, C. M. Suto, P. J. A. Davies, R. A. Heyman and A. M. Nadzan. 1995. Design and synthesis of potent retinoid X receptor selective ligands that induce apoptosis in leukemia cells. J. Med. Chem. 38:31463155.

Breslow, "Mouse models of atherosclerosis," Science, 272:685–688, 1996.

Brooks-Wilson et al. "Mutations in ABC1 in Tangier disease and familial high-density lipoprotein deficiency," Nat. Genet. 22:336–345, 1999.

Brown, and Goldstein, "The SREBP pathway: regulation of cholesterol metabolism by proteolysis of a membrane-bound transcription factor," Cell, 89:331–340, 1997.

Brown, Goldstein, "Lipoprotein metabolism in the macrophage: implications for cholesterol deposition in atherosclerosis," Annu. Rev. Biochem. 52:223–261, 1983.

Buchler et al., J. Biol Chem. 271:15091–15098, 1996.

Bucolo and David, "Quantitative determination of serum triglycerides by the use of enzymes," Clin. Chem., 19:476–482, 1973.

Bugge et al., EMBO J., 11:1409–1418, 1992.

Caldovic and Hackett Jr., "Development of position-independent expression vectors and their transfer into transgenic fish," Mol. Mar. Biol. Biotechnol., 4(1):51–61, 1995.

Carey and Duane, "Enterohepatic circulation," In: The Liver Biology and Pathobiology, Arias, Boyer, Fausto, Jakoby, Schachter, Shafritz, (eds), New York Raven Press Ltd., pp. 719–767, 1994.

Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," Biotechnology NY, 11(11): 1263–1270, 1993.

Chalfie et al., Science, 263:802–805, 1994.

Chang et al., "Foreign gene delivery and expression in hepatocytes using a hepatitis B virus vector," Hepatology, 14:134A, 1991.

Chen and Okayama, "High-efficiency transfection of mamiminalian cells by plasmid DNA," Mol. Cell Biol., 7:2745–2752, 1987.

Chiang and Stroup, "Identification and characterization of a putative bile acid-responsive element in cholesterol 7(x-hydroxylase gene promoter," J. Biol. Cliem., 269:17502–17507, 1994.

Clark, Voulgaropoulou, Fraley, Johnson, "Cell lines for the production of recombinant adeno-associated virus," Human Gene Therapy, 6:1329–1341, 1995.

Coffin, "Retroviridae and their replication," In: Virology, Fields et al. (eds.), New York: Raven Press, pp. 1437–1500, 1990.

Cohen, Raicht, Mosbach, "Sterol metabolism studies in the rat. Effect of primary bile acids (sodium taurochenodeoxycholate and sodium taurocholate) on sterol metabolism," J. Lipid Res., 18:223–231, 1977.

Colberre-Garapin et al., J. Mol. Biol., 150:1, 1981.

Cotten, Wagner, Zatloukal, Phillips, Curiel, "High efficiency receptor-mediated delivery of small and large (48 kilobase) gene constructs using the endosome disruption activity of defective or inactivated adenovirus particles," P.N.A.S. USA, 89:6094–6098, 1992.

Couch et al., "Immunization with types 4 and 7 adenovirus by selective infection of the intestinal tract." Am. Rev. Resp. Dis., 88:394403, 1963.

Coupar et al., "A general method for the construction of recombinant vaccinia virus expressing multiple foreign genes," Gene, 68:1–10, 1988.

Cozzi, Tucker, Langford, Pino-Chavez, Wright, O'Connell, Young, Lancaster, McLanghlin, Hunt, Bordin, White, "Characterization of pigs transgenic for human decay-accelerating factor," Transplantation, 64(10): 1383–1392, 1997.

Curiel, "Gene transfer mediated by adenovirus-polylysine DNA complexes," In: Viruses in Human Gene Therapy, J.-M. H. Vos (Ed.), Carolina Academic Press, Durham, N.C., pp. 179–212, 1994.

Ebert, Selgrath, DiTulio, Denman, Smith, Memon, Schindler, Monastersky, Vitale, Gordon, "Transgenic production of a variant of human tissue-type plasminogen activator in goat milk: generation of transgenic goats and analysis of expression." Biotechnology NY, 9(9):835–838, 1991.

Fechheimer et al., "Transfection of mammalian cells with plasmid DNA by scrape loading and sonication loading," Proc. Nat'l Acad. Sci. USA, 84:8463–8467, 1987.

Ferkol et al., FASEB J., 7:1081–1091, 1993.

Field, F. J., E. Born, S. Murthy and S. N. Mathur. 1998. Caveolin is present in intestinal cells: role in cholesterol trafficking? J. Lipid Res. 39:1938–1950.

Flotte, Afione, Conrad, McGrath, Solow, Oka, Zeitlin, Guggino, and Carter, "Stable in vivo expression of the cystic fibrosis transmembrane conductance regulator with an adeno-associated virus vector," Proc. Natl. Acad. Sci. USA, 90:10613–10617, 1993.

Flotte, Barraza-Ortiz, Solow, Afione, Carter, and Guggino, "An improved system for packaging recombinant adeno-associated virus vectors capable of in vivo transduction," Gene Therapy, 2:29–37, 1995.

Flotte, Solow, Owens, Afione, Zeitlin, and Carter, "Gene expression from adeno associated virus vector in airway epithelial cells," Am. J. Respir. Cell Mol. Biol., 7:349–356, 1992.

Forman et al., Cell, 81:541–550, 1995c.

Forman et al., Cell, 81:687–693, 1995a.

Forman et al., Cell, 83(5):803–812, 1995b.

Forman et al., Mol. Endocrinol., 3:1610–1626, 1989.

Fraley et al., "Entrapment of a bacterial plasmid in phospholipid vesicles: Potential for gene transfer," Proc. Nat'l Acad. Sci. USA, 76:3348–3352, 1979.

Francis, Knopp, and Oram, J. F. "Defective removal of cellular cholesterol and phospholipids by apolipoprotein A-1 in Tangier disease," J. Clin. Invest. 96:78–87, 1995.

Franz, Mueller, Haartong, Frey, Katus, "Transgenic animal models: new avenues in cardiovascular physiology," J. Mol. Med., 75(2):115–119, 1997.

Friedmann, "Progress toward human gene therapy." Science, 244:1275–1281, 1989.

Ghosh and Bachhawat, "Targeting of liposomes to hepatocytes," In: Liver diseases, targeted diagnosis and therapy using specific receptors and ligands," Wu G. and C. Wu ed. New York: Marcel Dekker, pp. 87–104, 1991.

Ghosh-Choudhury et al., "Protein IX, a minor component of the human adenovirus capsid, is essential for the packaging of full-length genomes," EMBO J., 6:1733–1739, 1987.

Ghosh-Choudhury et al., "Protein IX, a minor component of the human adenovirus capsid, is essential for the packaging of full-length genomes," EMBO J., 6:1733–1739, 1987.

Glass, C. K, Endocrinol. Rev., 15:391–407, 1994.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Gopal, "Gene transfer method for transient gene expression, stable transfection, and cotransfection of suspension cell cultures," *Mol. Cell Biol.*, 5:1188–1190, 1985.

Gottesman, Pastan, *Annu. Rev. Biochem.* 62:385–427, 1993.

Graham and Prevec, "Adenovirus-based expression vectors and recombinant vaccines," *Biotechnology*, 20:363–390, 1992.

Graham and Prevec, "Manipulation of adenovirus vector," In: *Methods in Molecular Biology: Gene Transfer and Expression Protocol*, E. J. Murray (ed.), Clifton, N.J.: Humana Press, 7:109–128, 1991.

Graham and van der Eb, "A new technique for the assay of infectivity of human adenovirus 5 DNA", *Virology*, 52:456467, 1973.

Graham et al., "Characteristics of a human cell line transformed by DNA from human adenovirus type 5", *J. Gen. Virol.*, 36:59–72, 1977.

Graham et al., "Characteristics of a human cell line transformed by DNA from human adenovirus type 5", *J. Gen. Virol.*, 36:59–72, 1977.

Grunhaus and Horwitz, "Adenovirus as cloning vector," *Seminar in Virology*, 3:237–252, 1992.

Harland and Weintraub, "Translation of mammalian mRNA injected into Xenopus oocytes is specifically inhibited by antisense RNA," *J. Cell Biol.*, 101: 1094–1099, 1985.

Haskell and Bowen, "Efficient production of transgenic cattle by retroviral infection of early embryos," *Mol. Reprod. Dev.*, 40(3):386–390, 1995.

Hermonat and Muzyczka, "Use of adeno-associated virus as a mammalian DNA cloning vector; transduction of neomycin resistance into mammalian tissue culture cells," *Proc. Natl. Acad. Sci. USA*, 81:64666470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l Acacd. Sci. USA* 90:2812–2816, 1993.

Higgins, "ABC transporters: from microorganisms to man," *Annu. Rev. Cell Biol.* 8:67–113, 1992.

Homan, R. and B. R. Krause. 1997. Established and emerging strategies for the inhibition of cholesterol absorption. Curr. Pharmaceut. Design 3:2944.

Horwich et al. "Synthesis of hepadenovirus particles that contain replication-defective duck hepatitis B virus genomes in cultured HuH7 cells," *J. Virol.*, 64:642–650, 1990.

Ishibashi, Brown, Goldstein, Genrard, Hammer, Herz, "Hypercholesterolemia in low density lipoprotein receptor knockout mice and its reversal by adenovinus-mediated gene delivery," *J. Clin. Invest.*, 92:883–893, 1993.

Ishibashi, Schwarz, Frykman, Herz, Russell, "Disruption of cholesterol 7α-hydroxylase gene in mice. I. Postnatal lethality reversed by bile acid and vitamin supplementation," *J. Biol. Chem.*, 271:18017–18023, 1996.

Janowski, Wi lly, Rama-Devi, Falck, Mangelsdorf, "An oxysterol signaling pathway mediated by the nuclear receptor LXRα," *Nature*, 383:728–731, 1996.

Jeske, D. J. and J. M. Dietschy. 1980. Regulation of rates of cholesterol synthesis in vivo in the liver and carcass of the rat measured using [3H]water. J. Lipid Res. 21:364–376.

Jones and Shenk, "Isolation of deletion and substitution mutants of adenovirus type 5," *Cell*, 13:181–188, 1978.

Kaneda et at., "Increased expression of DNA cointroduced with nuclear protein in adult rat liver," *Science*, 243:375–378, 1989.

Kang, Cho, Kole, "Up-regulation of luciferase gene expression with antisense oligonucleotides: implications and applications in functional assay development," *Biochetemistry*, 37(18):6235–6239, 1 998.

Kaplitt, Leone, Samulski, Siao, Pfaff, O'Malley, During, "Long-term gene expression and phenotypic correction suing adeno-associated virus vectors in the mammalian brain," *Nature Genetics*, 8:148–154; 1994.

Karisson et at, EMBO J., 5:2377–2385, 1986.

Kato et al., "Expression of hepatitis β virus surface antigen in adult rat liver," *J. Biol. Chem.*, 266:3361–3364, 1991.

Kaufman, "Selection and Coamplification of Heterologous Genes in Mammalian Cells," *Methods in Enzymology*, 185:537–566, 1990.

Kelleher and Vos, "Long-term episomal gene delivery in human lymphoid cells using human and avian adenoviral-assisted transfection," *Biotechniques*, 17(6):1110–1117, 1994.

Klein et al., "High-velocity microprojectiles for delivering nucleic acids into living cells," *Nature*, 327:70–73, 1987.

Kliewer et al., *Nature*, 355:446–449, 1992a.

Kliewer et al., *Nature*, 358:771–774, 1992b.

Kliewer, Fomman, Blumberg, Ong, Borgmeyer, Mangelsdorf, Umesono, Evans, "Differential expression and activation of a family of marine peroxisome proliferator-activated receptors," *Proc. Natl. Acad. Sci. USA*, 91:735–7359, 1994.

Kotin, Siniscalco, Samulski, Zhu, Hunter, McLaughlin, Muzyczka, Berns, "Site-specific integration by adeno-associated virus," *Proc. Natl. Acad. Sci. USA*, 87:2211–2215, 1990.

Kurokawa et al., *Genes Dev.*, 7:1423–1435, 1993.

Kurokawa et al., *Nature*, 371:528–531, 1 994.

Kurokawa et al., *Nature*, 377:451–454, 1995.

Labosky, Barlow, Hogan, "Mouse embryonic germ (EG) cell lines: transmission through the germline and differences in the methylation imprint of insulin-like growth factor 2 receptor (lgf2r) gene compared with embryonic stem (ES) cell lines," *Developtnent*, 120:3197–3204, 1994.

LaFace, Hermonat, Wakeland, Peck, "Gene transfer into hematopoietic progenitor cells mediated by an adeno- associated virus vector," *Virology*, 162:483–486, 1988.

Langmann et al. "Molecular cloning of the human ATP-binding cassette transporter I (hABC1): evidence for sterol-dependent regulation in macrophages," Biochem. *Biophys. Res. Commun.* 257:29–33, 1999.

Laughlin, Cardellichio, Coon, "Latent Infection of KB Cells with Adeno-Associated Virus Type 2," *J. Virol.*, 60:515–524, 1986.

Lawn et al. "The Tangier disease gene product ABC1 controls the cellular apolipoprotein-mediated lipid removal pathway," *J. Clin. Invest.* 104: R25–R31, 1999.

Le Gal La Salle et al., "An adenovirus vector for gene transfer into neurons and glia in the brain," *Science*, 259:988–990, 1993.

Lebkowski, McNally, Okarna, and Lerch, "Adeno-associated virus: a vector system for efficient introduction and integration of DNA into a variety of mammalian cell types," *Mol. Cell. Biol.*, *:3988–3996, 1988.

Leblanc & Stunnenberg, *Genes Dev.*, 9:1811–1816, 1995.

Lehmann, Kliewer, Moore, Smith-Oliver, Oliver, Su, Sundseth, Winegar, Blanchard, Spencer, Willson, "Activation of the nuclear receptor LXR by oxysterols defines a new hormone response pathway," *J. Biol. Chem.*, 272:3137–3140, 1997.

Lehrman, Russell, Goldstein, Brown, Alu-Alu recombination deletes splice acceptor sites and produces secreted low density lipoprotein receptor in a subject with familial hypercholesterolemia," *J. Biol. Chem.*, 262:3354–3361, 1987.

Leid et al., *Cell*, 68:377–395, 1992b.

Leid et al., *Trends Biochem Sci.*, 17:427–433, 1992a.

Levrero et al., "Defective and nondefective adenovirus vectors for expressing foreign genes in vitro and in vivo," *Gene*, 101: 195–202, 1991.

Luo, Zhou, Cooper, Munshi, Boswell, Broxmeyer, Srivastava, "Adeno-associated virus 2 mediated transfer and functional expression of a gene encoding the human granulocyte-macrophage colony-stimulating factor," *Blood*, 82 (Supp.): 1,303A, 1994.

Mangelsdorf et al., *Cell*, 66:555–561, 1991.

Mangelsdorf et al., *Genes Dev.*, 6:329–344, 1992.

Mangelsdorf et al., *Nature*, 345:224–229, 1990.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Marks et al., *EMBO J.*, 11:1419–1435, 1992.

McCarty, Christensen, Muzyczka, "Sequences Required for Coordinate Induction of Adeno-Associated Virus p19 and p40 Promoters by Rep Protein," *J. Virol.*, 65:2936–2945, 1991.

McLaughlin, Collis, Hermonat, Muzyczka, "Adeno-Associated Virus General Transduction Vectors: Analysis of Proviral Structures," *J. Virot.*, 62:1963–1973, 1988.

Michaelis, *Semin. Cell Biol.* 4:17–27, 1993.

Mitchell, J. R., *Schweiz. Med. Wochenschr.*, 120(11):359–364, Mar. 17, 1990.

Mori, Tsukamoto, Mori, Tashiro, Fujiki, "Molecular cloning and deduced amino acid sequence of nonspecific lipid transfer protein (sterol carrier protein 2) of rat liver a higher molecular mass (60 kDa) protein contains the primary sequence of nonspecific lipid transfer protein as its C-terminal part," *Proc. Natl. Acad. Sci. USA*, 88:4338–4342, 1991.

Mukherjee et al., *Arterinoscler. Thromb. Vasc. Biol.*, 18:272–276. 1998.

Muzyczka, "Use of Adeno-Associated Virus as a General Transduction Vector for Mammalian Cells," *Curr. Top. Microbiol. Immunol.*, 158:97–129, 1992.

Nicolas and Rubinstein, "Retroviral vectors," In: *Vectors: A survey of molecular cloning vectors and their uses*, Rodriguez and Denhardt (eds.), Stoneham: Butterworth, pp. 494–513, 1988.

Nicolau and Sene, "Liposome-mediated DNA transfer in eukaryotic cells," *Biochem. Biophys. Acta*, 721:185–190, 1982.

Ohi, Dixit, Tillery, and Plonk, "Construction and replication of an adeno-associated virus expression vector that contains human λ-globin cDNA," *Gene*, 89L:279–282, 1990.

Ono, Hirose, Miyazaki, Yamamoto, Matsumoto, "Transgenic medaka fish bearing the mouse tyrosinase gene: expression and transmission of the transgene following electroporation of the orange-colored variant," *Pigment Cell Res.*, 10(3):168–175, 1997.

Osono, Woollett, Herz, Dietscht, "Role of low density lipoprotein receptor in the flux of cholesterol through the plasma and across the tissue of the mouse," *J. Clin. Invest.*, 95:1124–1132, 1995.

Paskind et al., "Dependence of moloney murine leukemia virus production on cell growth," *Virology*, 67:242–248, 1975.

Peet, D. J., B. A. Janowski, and D. J. Mangelsdorf. 1998b. The LXRs: a new class of oxysterol receptors. Curr. Opin. Genet. Dev. 8:571–575.

Peet, D. J., S. D. Turley, W. Ma, B. A. Janowski, J.-M. A. Lobaccaro, R. E. Hammer, and D. J. Mangelsdorf. 1998a. Cholesterol and bile acid metabolism are impaired in mice lacking the nuclear oxysterol receptor LXRα. Cell 93:693–704.

Pelletier and Sonenberg, *Nature*, 334:320–325, 1988.

Perales et al., *Proc. Natl. Acad. Sci. USA*, 91:4086–4090, 1994.

Pericak-Vance and Haines, "Genetic susceptibility to alzheimer disease," *Trends Genet.*, 11:504–508, 1995.

Perlmann & Jansson, *Genes Dev.*, 9:769–782, 1995.

Perlmann et al., *Genes Dev.*, 7:1411–1422, 1993.

Pinto-Sietsma and Paul, "Transgenic rats as models for hypertension," *J. Hum. Hypertens.*, 11 (9):577–581, 1997.

Potter et at., "Enhancer-dependent expression of human k immunoglobulin genes introduced into mouse pre-B lymphocytes by electroporation," *Proc. Nat'l Acad. Sci. USA*, 81:7161–7165, 1984.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Renan, "Cancer genes: current status, future prospects, and applicants in radiotherapy/oncology," *Radiother. Oncol.*, 19:197–218, 1990.

Renan, "Cancer genes: current status, future prospects, and applicants in radiotherapy/oncology," *Radiotiler. Oncol.*, 19:197–218, 1990.

Rich et al., "Development and analysis of recombinant adenoviruses for gene therapy of cystic fibrosis," *Hum. Gene Ther.*, 4:461–476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rosahl, Geppert, Spillane, Herz, Hammer, Malenka, S üdhof, "Short-term synaptic plasticity is altered in mice lacking synapsin 1," *Cell*, 75:661–670, 1993.

Rosenfeld et al., "Adenovirus-mediated transfer of a recombinant al-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class H antigens by mouse ecotropic murine leukemia virus-derived viruses," *Proc. Natl. Acad. Sci. USA*, 86:9079–9083, 1989.

Rudling, "Hepatic mRNA levels for the LDL receptor and HMG-CoA reductase show coordinate regulation in vivo," *J. Lipid Res.*, 33:493–501, 1992.

Ruetz, Gros, *Cell* 77:1071–1081, 1994.

Russell and Setchell, "Bile acid biosynthesis," *Biochemistry*, 31, 47374749, 1992.

Rust et al. "Tangier disease is caused by mutations in the gene encoding ATP-binding cassette transporter 1," *Nat. Genet.* 22:352–355, 1999.

Samulski, Chang, Shenk, "Helper-free stocks of recombinant adeno-associated viruses: Normal integration does not require viral gene expression," *J. Virol.*, 63:3822–3828, 1989.

Samulski, Zhu, Xiao, Brook, Housman, Epstein, Hunter, "Targeted integration of adeno-associated virus (AAV) into human chromosome 19, " *EMBO J.*, 10:3941–3950, 1991.

Santerre, et al., *Gene*, 30:147, 1984

Savary et al. *Genomics* 41:275–275, 1997.

Schultheis, A. H., *Nurse Pract.*, 15(1):4046, Jan. 1990.

Schwartz, M., D. W. Russell, J. M. Dietschy, and S. D. Turley. 1998. Marked reduction in bile acid synthesis in cholesterol 7a-hydroxylase-deficient mice does not lead to diminished tissue cholesterol turnover or to hypercholesterolemia. J. Lipid Res. 39:1833–1843.

Schwarz, Lund, Lathe, Björkhem, Russell, "Identification and characterization of a mouse oxysterol 7α-hydroxylase cDNA," *J. Biol. Chem.*, 272:23995–24001, 1997.

Shelling and Smith, "Targeted integration of transfected and infected adeno-associated virus vectors containing the neomycin resistance gene," *Gene Therapy*, 1:165–169, 1994.

Shimano, Horton, Hammer, Shimomura, Brown, Goldstein, "Overproduction of cholesterol and fatty acids causes massive liver enlargement in transgenic mice expressing truncated SREBP-1a," *J. Clin. Invest.*, 98:1575–1584, 1996.

Shimano, Shimomura, Hammer, Herz, Goldstein, Brown, Horton, "Elevated levels of SREBP-2 and cholesterol synthesis in livers of mice homozygous for a targeted disruption of the SREBP-1 gene," *J. Clin. Invest.*, 100:21152124, 1997.

Stratford-Perricaudet and Perricaudet, "Gene transfer into animals: the promise of adenovirus," *In: Human Gene Transfer*, Eds, O. Cohen-Haguenauer and M. Boiron, Editions John Libbey Eurotext, France, p. 51–61, 1991.

Stratford-Perricaudet et al., "Evaluation of the transfer and expression in mice of an enzyme-encoding gene using a human adenovirus vector," *Hum. Gene Ther.*, 1:241–256, 1990.

Tall, "An overview of reverse cholesterol transport," *Eur. Heart J.* 19(Suppl. A): A31–A35, 1998.

Temin, "Retrovirus vectors for gene transfer: Efficient integration into and expression of exogenous DNA in vertebrate cell genome," *In: Gene Transfer*, Kucherlapati (ed.), New York, Plenum Press, pp. 149–188, 1986.

Top et al., "Immunization with live types 7 and 4 adenovirus vaccines. II. Antibody response and protective effect against acute respiratory disease due to adenovirus type 7, " *J. Infect. Dis.*, 124:155–160, 1971.

Tratschin, Miller, Smith, Carter, "Adeno-associated virus vector for high-frequency integration, expression and rescue of genes in mammalian cells," *Mol. Cell. Biol.*, 5:32581–3260, 1985.

Tratschin, West, Sandbank, Carter, "A human parvovirus, adeno-associated virus, as a eucaryotic vector: transient expression and encapsidation of the procaryotic gene for chloramphenicol acetyltransferase," *Mol. Cell. Biol.*, 4:2072–2081, 1984.

Tur-Kaspa et al., "Use of electroporation to introduce biologically active foreign genes into primary rat hepatocytes," *Mol. Cell Biol.*, 6:716–718, 1986.

Turley and Dietschy, "The metabolism and excretion of cholesterol by the liver, " *In: Tile Liver Biology and Pathobiology*, Arias, Jakoby, Popper, Schachter, Shafritz (eds.), New York: Raven Press, Ltd., pp. 617–641, 1988.

Turley, S. D, B. P. Daggy, and J. M Dietschy. 1994. Psyllium augments the cholesterol-lowering action of cholestyramine in hamsters by enhancing sterol loss from the liver. Gastroenterology 107:444–452.

Turley, S. D., B. P. Daggy, and J. M. Dietschy. 1991. Cholesterol-lowering effect of psyllium mucilloid in the hamster: sites and possible mechanisms of action. Mechanism 40:1063–1073.

Turley, S. D., B. P. Daggy, and J. M. Dietschy. 1996. Effect of feeding psyllium and cholestyramine in combination on low density lipoprotein metbolism and fecal bile acid excretion in hamsters with dietary-induced hypercholesterolemia. J. Cardiovasc. Pharmacol. 27:71–79.

Turley, S. D., J. M. Anderson, and J. M. Dietschy. 19R1. Rates of sterol synthesis and uptake in the major organs of the rat in vivo. J. Lipid Res. 22:551–569.

Turley, S. D., M. W. Hemdon, and J. M. Dietschy. 1994. Reevaluation and application of the dual-isotope plasma ratio method for the measurement of intestinal cholesterol absorption in the hamster. J. Lipid Res. 35:328–339.

Turley, Spady, Dietschy, "Regulation of fecal bile acid excretion in male golden Syrian hamsters fed a cereal-based diet with and without added cholesterol," *Hepatology*, 25:797–803, 1997.

Uchida, Nomura, Takeuchi, Effects of cholic acid, chenodeoxycholic acid and their related bile acids on cholesterol, phospholipid and bile acid levels in serum, liver, bile and feces of rats," *J. Biochem.*, 87:187–194, 1980.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.*, 6(3):203–212, 1997.

Wagner et al., *Science*, 260:1510–1513, 1990.

Wahlstrom et al., *Mol. Endrocrinol.*, 6:1013–1022, 1992.

Walsh, Nienhuis, Samulski, Brown, Miller, Young, Liu, "Phenotypic correction of Fanconi anemia in human hematopoietic cells with a recombinant adeno-associated virus vector," *Proc. Natl. Acad. Sci. USA*, 89:7257–7261, 1994; *J. Clin. Invest.*, 94:1440–1448, 1994.

Watanabe, M., Shirayoshi, Y., Koshimizu, U., Hashimoto, S., Yonehara, S., Eguchi, Y., Tsujimoto, Y. and Nakatsuji, N., "Gene transfection of mouse primordial germ cells in vitro and analysis of their survival and growth control," *Exp. Cell Res.* 230:76–83, 1997.

Wei, Wei, Samulski, Barranger, "Expression of the human glucocerebrosidase and arylsulfatase A genes in murine and patient primary fibroblasts transduced by an adeno-associated virus vector," *Gene Therapy*, 1:261–268, 1994.

Welsh, Smith, *Cell* 73:1251–1254, 1993.

Willy and Mangelsdorf, "Nuclear orphan receptors: the search for novel ligands and signaling pathways," *In: Hormones and Signaling*, Volume 1, O'Malley, (ed.), San Diego: Academic Press, pp. 307–358, 1998.

Willy et al., *Genes Dev.*, 9:1033–1045, 1995.

Willy, P. J., K. Umesono, E. S. Ong, R. M. Evans, R. A. Heyman and D. J. Mangelsdorf. 1995. LXR, a nuclear receptor that defines a distinct retinoid response pathway. Genes Dev. 9:1033–1045.

Willy, Umesono, Ong, Evans, Heyman, Mangelsdorf, "LXR, a nuclear receptor that defines a distinct retinoid response pathway," *Genes Dev.*, 9:033–1045, 1995.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Yang et al., "in vivo and in vitro gene transfer to mammalian somatic cells by particle bombardment," *Proc. Nat'l Acad. Sci. USA*, 87:9568–9572, 1990.

Yang, Chen, Trempe, "Characterization of cell lines that inducibly express the adeno-associated virus Rep proteins," *J. Virol.*, 68:4847–4856, 1994.

Yeom, Fuhrmann, Ovitt, Brehm, Ohbo, Gross, Hübner, Schöler, "Germline regulatory element of Oct-4 specific for totipotent cycle of embryonal cells," *Development*, 122:881–894, 1996.

Yoder, Kang, Zhou, Luo, Srivastava, "in vivo gene transfer in murine hematopoietic reconstituting stem cells mediated by the adeno-associated virus 2-based vectors," *Blood*, 82 (Supp.): 1:347A, 1994.

Yokode, Hammer, Ishibashi, Brown, Goldstein, (1990). Diet-induced hypercholesterolemia in mice: prevention by overexpression of LDL receptors," *Science*, 250,1273–1275, 1990.

Young and Fielding, "The ABCs of cholesterol efflux," *Nature Genetics* 22: 316–318, 1999.

Yu et al., *Cell*, 67:1251–1266, 1991.

Zechel et al., *EMBO J.*, 13:1425–1433, 1994.

Zhang et al., *Nature*, 355:441–446, 1992.

Zhou, Broxmyer, Cooper, Harrington, Srivastava, "Adeno-associated virus 2 mediated gene transfer in murine hematopoietic cells, *Exp. Hentatol.* (NY), 21:928–933, 1993.

Zhou, Cooper, Kang, Ruggieri, Heimfeld, Srivastava, Broxmeyer, "Adeno-associated virus 2-mediated high efficiency gene transfer into immature and mature subsets of hematopoietic progenitor cells in human umbilical cord blood," *J. Exp. Med.*, 179:1867–1875, 1994.

What is claimed is:

1. A transgenic mouse, the cells of which comprise at least one endogenous altered LXRα allele, wherein said altered LXRα allele comprises the insertion of a selectable marker gene, wherein said mouse shows a phenotype of increased hepatic cholesterol accumulation when fed a 2% cholesterol diet for seven days compared to a control mouse.

2. The transgenic mouse or claim 1, wherein a transcript produced from said endogenous altered LXRα allele contains an interruption in the LXRα coding sequence.

3. The transgenic mouse of claim 1, wherein said endogenous altered LXRα allele contains a nonsense mutation that truncates the corresponding encoded LXRα polypeptide.

4. The transgenic mouse of claim 1, wherein said endogenous altered LXRα allele contains a deletion of LXRα coding sequences.

5. The transgenic mouse of claim 1, wherein said endogenous altered LXRα allele contains a mutation in the 5' regulatory region of the LXRα gene.

6. The transgenic mouse of claim 5, wherein said alteration comprises substitution of an inducible/repressable promoter for the endogenous LXRα promoter.

7. The transgenic mouse of claim 1, wherein said cells comprise two endogenous altered LXRα alleles, wherein said altered LXRα alleles both comprise the insertion of a selectable marker gene, and wherein said mouse shows a phenotype of hepatomegaly when fed a 2% cholesterol diet for ninety days.

8. The transgenic mouse of claim 7, wherein a transcript produced from said endogenous altered LXRα alleles both contain an interruption in the LXRα coding sequences.

9. Th transgenic mouse of claim 7, wherein said endogenous altered LXRα alleles both contain at nonsense mutation that truncates the corresponding encoded LXRα polypeptide.

10. The transgenic mouse or claim 7, wherein said endogenous altered LXRα alleles both contain a deletion of LXRα coding sequences.

11. The transgenic mouse of claim 7, wherein said altered endogenous LXRα alleles both containing a mutation in the 5' regulatory region of the LXRα genes.

12. The transgenic mouse of claim 11, wherein said alterations comprise substitutional of inducible/repressible promoters for both of the endogenous LXRα promoters.

13. A method for screening a candidate substance for the ability to reduce cholesterol levels via LXRα in a mammal comprising:

(a) providing a transgenic mouse, the cells of which comprise at least one endogenous altered LXRα allele, wherein said altered LXRα allele comprises the insertion of a selectable marker gene;

(b) treating said mouse with said candidate substance; and (c) monitoring a cholesterol-related phenotype in said mouse, wherein a reduction in said cholesterol-related phenotype in said mouse treated with said candidate substance, as compared to a similar mouse not treated with said candidate substance, indicates that said candidate substance reduces cholesterol levels via an LXRα-independent mechanism.

14. The method of claim 13, wherein said phenotype is cholesterol absorption, circulating cholesterol, hepatic cholesterol, hepatomegaly, atherosclerosis, cardiac failure, cardiac (atrophy/hypertrophy), activity level, survival, cancer, reproduction, immune function, skin disease, cognitive function, and adrenal function.

15. The method of claim 13, wherein said mouse is maintained on a high cholesterol diet.

16. The method of claim 13, wherein said mouse further is treated with an agent that blocks cholesterol biosynthesis.

17. The method of claim 13, wherein said cells comprise two endogenous altered LXRα alleles, each allele comprising the insertion of a selectable marker gene.

18. A method for screeching a candidate substance for the ability to increase bile acid synthesis via LXRα in a mammal comprising:

(a) providing a transgenic mouse, the cells of which comprise at least one endogenous altered LAXα allele, wherein said altered LXRα allele comprises the insertion of a selectable marker gene;

(b) treating said mouse with said candidate substance; and (c) monitoring a bile acid-related phenotype in said mouse, wherein an increase in said bile acid-related phenotype in said mouse treated with said candidate substance, as compared to a similar mouse not treated with said candidate substance, indicates that said candidate substance increases bile acid synthesis via an LXRα-independent mechanism.

19. The method of claim 18, wherein said bite acid-related phenotype is selected from the group consisting of cholesterol level, Cyp7a synthesis, fecal bile acid excretion, bile acid pool size and bile acid composition.

20. A isolated transgenic mouse cell which comprises at least one endogenous altered LXRα allele, wherein said altered LXRα allele comprises the insertion of a selectable marker gene.

21. The isolated transgenic cell of claim 20, wherein said cell comprises two endogenous altered LXRα alleles, wherein said altered LXRα alleles both comprise the insertion of a selectable marker gene.

* * * * *

UNITED STATES PATENT AND TRADEMARK OFFICE
CERTIFICATE OF CORRECTION

PATENT NO. : 6,835,866 B1
DATED : December 28, 2004
INVENTOR(S) : David J. Mangelsdorf et al.

It is certified that error appears in the above-identified patent and that said Letters Patent is hereby corrected as shown below:

<u>Title page,</u>
Item [75], Inventors, please delete "Joyce J. Repa, Dallas, TX (US);";
please insert -- "Daniel J. Peet, Dallas, TX (US); -- and -- Jean-Marc A. Lobaccaro, Dallas, TX (US); --

<u>Column 57,</u>
Line 1, "or" should read -- of --.
Line 2, "substitutional" should read -- substitution --.

<u>Column 58,</u>
Line 5, "LAXα" should read -- LXRα --.

Signed and Sealed this

Nineteenth Day of July, 2005

JON W. DUDAS
*Director of the United States Patent and Trademark Office*

```
                             SEQUENCE LISTING

<160> NUMBER OF SEQ ID NOS: 5

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ttaagctttg tcccgggcat tccaactgg                                         29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ttgaattcga cttggtgagc accaacacat                                        30

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
aagaagcttg aagaggaagg ggaa                                              24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
agcttagctt tgtccggctg aag                                               23

<210> SEQ ID NO 5
<211> LENGTH: 25
```

```
-continued
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
gctttggtca ctcaagttca agtta                                              25
```